US009605077B2

(12) United States Patent
Arlen et al.

(10) Patent No.: US 9,605,077 B2
(45) Date of Patent: *Mar. 28, 2017

(54) RECOMBINANT MONOCLONAL ANTIBODIES AND CORRESPONDING ANTIGENS FOR COLON AND PANCREATIC CANCERS

(71) Applicant: PRECISION BIOLOGICS, INC., Rockville, MD (US)

(72) Inventors: Myron Arlen, Great Neck, NY (US); J. Andrew Bristol, Rockville, MD (US); Ariel Hollinshead, Rockville, MD (US); Kwong Tsang, Bethesda, MD (US)

(73) Assignee: Precision Biologics, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/739,701

(22) Filed: Jun. 15, 2015

(65) Prior Publication Data

US 2015/0353644 A1 Dec. 10, 2015

Related U.S. Application Data

(60) Division of application No. 13/012,679, filed on Jan. 24, 2011, now Pat. No. 9,169,326, which is a division of application No. 12/825,022, filed on Jun. 28, 2010, now Pat. No. 8,535,667, which is a continuation of application No. 12/000,701, filed on Dec. 17, 2007, now Pat. No. 7,763,720, which is a division of application No. 11/404,566, filed on Apr. 14, 2006, now Pat. No. 7,314,622.

(60) Provisional application No. 60/671,481, filed on Apr. 15, 2005.

(51) Int. Cl.
| | | |
|---|---|---|
| *C07K 16/30* | (2006.01) | |
| *A61K 39/395* | (2006.01) | |
| *A61K 45/06* | (2006.01) | |
| *C07H 21/04* | (2006.01) | |
| *A61K 39/00* | (2006.01) | |

(52) U.S. Cl.
CPC .... *C07K 16/3076* (2013.01); *A61K 39/39558* (2013.01); *A61K 45/06* (2013.01); *C07H 21/04* (2013.01); *C07K 16/303* (2013.01); *C07K 16/3046* (2013.01); *A61K 2039/505* (2013.01); *A61K 2039/507* (2013.01); *C07K 2316/96* (2013.01); *C07K 2317/24* (2013.01); *C07K 2317/565* (2013.01); *C07K 2317/73* (2013.01); *C07K 2317/732* (2013.01)

(58) Field of Classification Search
CPC .............. C07K 16/303; C07K 16/3046; C07K 16/3076

USPC ........... 424/133.1, 156.1; 530/387.3, 388.85, 530/391.3, 391.7
See application file for complete search history.

(56) References Cited

U.S. PATENT DOCUMENTS

| | | | |
|---|---|---|---|
| 4,810,781 A | 3/1989 | Hollinshead et al. | |
| 5,431,897 A | 7/1995 | Welt et al. | |
| 5,530,101 A | 6/1996 | Queen et al. | |
| 5,688,657 A | 11/1997 | Tsang et al. | |
| 5,712,369 A | 1/1998 | Old et al. | |
| 5,851,526 A | 12/1998 | Welt et al. | |
| 6,190,640 B1 | 2/2001 | Welt et al. | |
| 6,291,235 B1 | 9/2001 | Welt et al. | |
| 6,307,026 B1 | 10/2001 | King et al. | |
| 6,652,853 B2 | 11/2003 | Welt et al. | |
| 7,125,689 B2 | 10/2006 | Carr et al. | |
| 7,314,622 B2 * | 1/2008 | Arlen ..................... | C07H 21/04 424/133.1 |
| 7,763,720 B2 | 7/2010 | Arlen et al. | |
| 9,169,326 B2 * | 10/2015 | Arlen ..................... | C07H 21/04 |
| 2003/0031671 A1 | 2/2003 | Welt et al. | |
| 2003/0040027 A1 | 2/2003 | Ritter et al. | |
| 2007/0031327 A1 | 2/2007 | Luzzi et al. | |

FOREIGN PATENT DOCUMENTS

| | | |
|---|---|---|
| AU | 2006236508 | 5/2012 |
| IN | 247461 | 4/2011 |
| JP | 5039027 | 7/2012 |
| WO | 2004/003019 A2 | 6/2004 |
| WO | 2006/113546 | 10/2006 |

OTHER PUBLICATIONS

Beckman et al. (Can. 109:170-179 (2007)).
Casset et al. ((2003) BBRC 307, 198-205).
Cespedes et al. (Clin. Transl. Oncol. 8(5):318-329 (2006)).
Chen et al. J. Mol. Bio. (1999) 293, 865-881.
Dennis (Nature 442:739-741 (2006)).
De Pascalis et al. The Journal of Immunology (2002) 169, 3076-3084.
Fujimori et al. (J. Nuc. Med. 31:1191-1198 (1990)).
Holm et al ((2007) Mol. Immunol. 44: 1075-1084).

(Continued)

Primary Examiner — Lynn Bristol
(74) Attorney, Agent, or Firm — LeClairRyan, a professional corporation; Robin L. Teskin

(57) ABSTRACT

The present invention provides for purified or highly pure recombinant monoclonal antibodies that bind to human colorectal and pancreatic carcinoma-associated antigens (CPAA), along with nucleic acid sequences encoding the antibody chains, and the amino acid sequences corresponding to said nucleic acids and uses for said sequences.

18 Claims, 9 Drawing Sheets

(56) References Cited

OTHER PUBLICATIONS

Kumar et al. (J. Biol. Chem. 275:35129-35136 (2000)).
MacCallum et al. (J. Mol. Biol. (1996) 262:732-745).
Rudnick et al. (Can. Biotherp. & Radiopharm. 24: 155:162 (2009)).
Smith-Gill et al. (J. Immunol. 139:4135-4144 (1987)).
Song et al. (Biochem Biophys Res Comm 268:390-394 (2000)).
Talmadge et al. (Am. J. Pathol 170(3):793-804 (2007)).
Thurber et al. (Adv. Drug Deliv. Rev. 60:1421-1434 (2008)).
Vajdos et al. ((2002) J. Mol. Biol. 320, 415-428).
Voskoglou-Nomikos (Clin. Can. Res. 9:4227-4239 (2003)).
Ward et al. (Nature 341:544-546 (1989)).
Wu et al. (J. Mol. Biol. (1999) 294, 151-162.
Abken, et al. "Short DNA sequences from the cytoplasm of mouse tumor cells induce immortalization of human lymphocytes in vitro," Proc Natl Acad Sci U S A. Jul. 15, 1993;90(14):6518-22.
Arlen et al., "Abstract B124: Preclinical development of a novel therapeutic antibody to treat pancreas and colorectal cancers," Mol Cancer Ther 2009,8(12 Suppl);B124.
Arlen, et al. "The use of specific monoclonal antibodies to target immunogenic tumor membrane proteins in patients with recurrent pancreatic and colon cancer," Curr Drug Deliv. Jan. 2012;9(1):52-6. [Abstract].
Bristol et al., "Preclinical development of a novel therapeutic antibody to treat pancreas and colorectal cancers," Human Antibodies, vol. 19, No. 2-3, 2010, p. 36.
Burgess, et al. "Possible dissociation of the heparin-binding and mitogenic activities of heparin-binding (acidic fibroblast) growth factor-1 from its receptor-binding activities by site-directed mutagenesis of a single lysine residue," J Cell Biol. Nov. 1990;111(5 Pt 1):2129-38.
Fernsten, et al. "Characterization of the colorectal carcinoma-associated antigen defined by monoclonal antibody D612," Cancer Res. Feb. 1, 1991;51(3):926-34.
Genecards Profile for "Npc-1" 1-14 (Nov. 13, 2009).
Heath, et al. (1997) "The Human A33 Antigen Is a Transmembrane Glycoprotein and a Novel Member of the Immunoglobulin Superfamily" Proc. Natl. Acad. Sci. USA 94(2) : 469-474.
Herlyn, et al. "Monoclonal antibody detection of a circulating tumor-associated antigen. I. Presence of antigen in sera of patients with colorectal, gastric, and pancreatic carcinoma," J Clin Immunol. Apr. 1982;2(2):135-40.
Hollinshead, et al. (1970) "Skin-Reactive Soluble Antigen from Intestinal Cancer-Cell-Membranes and Relationship to Carcinoembryonic Antigens" Lancet 1(7658): 1191-1195.
Hollinshead, et al. (1972) "Separation of Skin Reactive Intestinal Cancer Antigen from the Carcinoembryonic Antigen of Gold" Science 177(52): 887-889.
Hollinshead, et al. (1985) "Specific Active Immunotherapy in Patients with Adenocarcinoma of the Colon Utilizing Tumor-Associated Antigens (TAA)" A Phase I Clinical Trial, Cancer 56: 480-489.
Hollinshead, et al. (Apr. 1973) "Further Comparison's of Separated Intestinal Cancer, Fetal Intestinal and Normal Intestinal Soluble Membrane Antigen and the Role of Tumor Related Antigens in the Diagnosis and Treatment of Intestinal Cancer" Proc. Second Intl. Symp. Cancer Detection and Prevention, Bologna, Italy, 616-620.
Johnstone, et al. (2000) "Characterization of Mouse A33 Antigen, a Definitive Marker for Basolateral Surfaces of Intestinal Epithelial Cells" Am. J. Physiol. Gastrointest. Liver Physiol. 279(3): G500-G510.
Kurihara, et al. (1979) "Soluble Membrane Antigens of Gastric Cancer Cells: An Analysis and Study of Activity in Inducing Cell-Mediated Immune Responses" J. Jap. Soc. Cancer Ther. 14(3): 313-324.
Lazar, et al. "Transforming growth factor alpha: mutation of aspartic acid 47 and leucine 48 results in different biological activities," Mol Cell Biol. Mar. 1988;8(3):1247-52.
Lin, et al. "Structure-function relationships in glucagon: properties of highly purified des-His-1-, monoiodo-, and (des-Asn-28, Thr-29)(homoserine lactone-27)-glucagon," Biochemistry. Apr. 22, 1975;14(8):1559-63.
Luka, et al. "Development of a serum biomarker assay that differentiates tumor-associated MUC5AC (NPC-1C Antigen) from normal MUC5AC," J Biomed Biotechnol. 2011;2011:934757.
Magnani, et al. "A monoclonal antibody-defined antigen associated with gastrointestinal cancer is a ganglioside containing sialylated lacto-N-fucopentaose II," J Biol Chem. Dec. 10, 1982;257(23):14365-9.
Ritter, et al. (1997) "Characterization of Posttranslational Modifications of Human A33 Antigen, a Novel Palmitoylated Surface Glycoprotein of Human Gastrointestinal Epithelium" Biochem. Biophys. Res. Commun. 236(3): 682-686.
Ritter, et al. (2001) "Serological Analysis of Human Anti-Human Antibody Responses in Colon Cancer Patients Treated with Repeated Doses of Humanized Monoclonal Antibody A33" Cancer Res. 61: 6851-6859.
Rudikoff, et al. "Single amino acid substitution altering antigen-binding specificity," Proc Natl Acad Sci U S A. Mar. 1982;79(6):1979-83.
Schwartz, et al. "A superactive insulin: [B10-aspartic acid]insulin(human)," Proc Natl Acad Sci U S A. Sep. 1987;84(18):6408-11.
Sears, et al. "Monoclonal antibody detection of a circulating tumor-associated antigen. I. Presence of antigen in sera of patients with colorectal, gastric, and pancreatic carcinoma," J Clin Immunol. Apr. 1982;2(2):135-40.
Shimano, et al. "Purification and characterization of a pancreatic cancer-associated antigen (PCAA) from normal colonic mucosa," Ann N Y Acad Sci. 1983;417:97-104.
The International Search Report Mailed Aug. 22, 2008.
Welt (2003) "Phase I Study of Anticolon Cancer Humanized Antibody A33" Clin. Cancer Res. 9: 1338-1346.

* cited by examiner

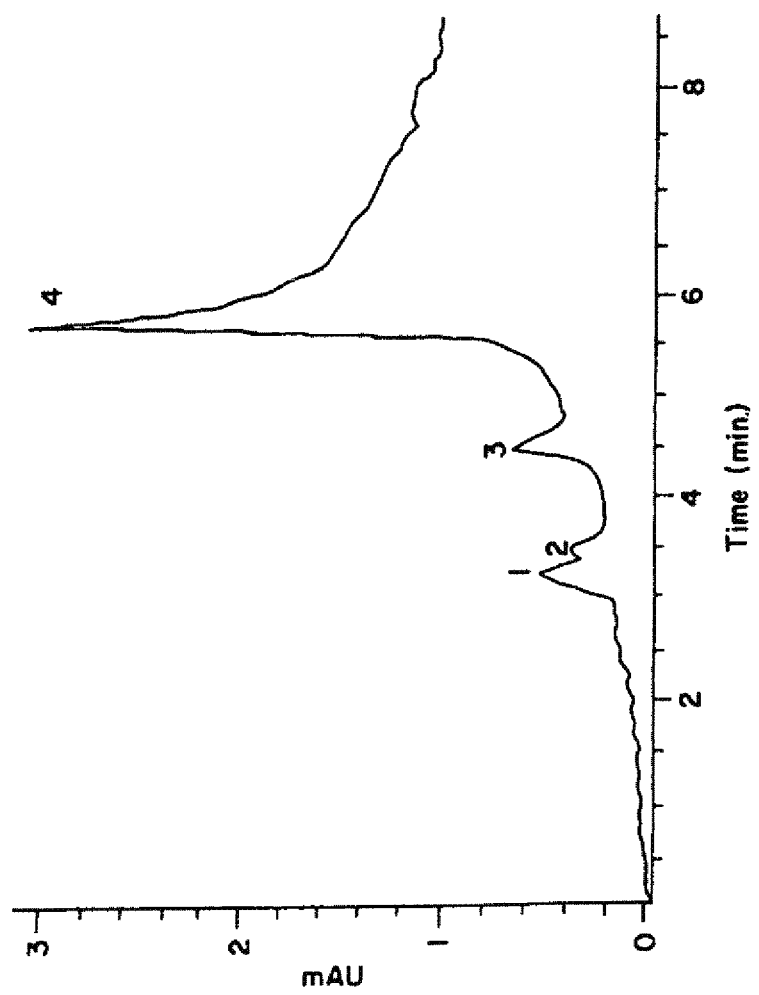

NPC-1 kappa light chain whole sequence. Translation start at 46. Length: 965
SEQ ID NO: 1

```
  1 ATGAGAATAC CATTAATTAG CTAGGGACCA AAATTCAAAG ACAAAATGGA
 51 TTTTCAGGTG CAGATTTTCA GCTTCCTGCT AATCAGTGCC TCAGTCATAC
101 TGTCCAGAGG ACAAGTTGTT CTCACCCAGT CTCCAGTAAT CATGTCTGCA
151 TCTCCAGGGG AGAAGGTCAC CATGACCTGC AGTGCCAGCT CAAGTATAAG
201 TTACATGTAC TGGTACCAGC AGAAGCCAGG CACCTCCCCC AAAAGATGGA
251 TTTATGACAC ATCCAAACTG GCTTCTGGAG TCCCTGCTCG CTTCAGTGGC
301 AGTGGGTCTG GGACCTCTTA TTCTCTCACA ATCAGCAACA TGGAGGCTGG
351 AGATGCTGCC ACTTATTACT GCCATCAGCG GGATTCTTAC CCATGGACGT
401 TCGGTGGAGG CACCAACCTG GAAATCAAAC GGGCTGATGC TGCACCAACT
451 GTATCCATCT TCCCACCATC CAGTGAGCAG TTAACATCTG GAGGTGCCTC
501 AGTCGTGTGC TTCTTGAACA ACTTCTACCC CAAAGACATC AATGTCAAGT
551 GGAAGATTGA TGGCAGTGAA CGACAAAATG GCGTCCTGAA CAGTTGGACT
601 GATCAGGACA GCAAAGACAG CACCTACAGC ATGAGCAGCA CCCTCACGTT
651 GACCAAGGAC GAGTATGAAC GACATAACAG CTATACCTGT GAGGCCACTC
701 ACAAGACATC AACTTCACCC ATTGTCAAGA GCTTCAACAG GAATGAGTGT
751 TAGAGACAAA GGTCCTGAGA CGCCACCACC AGCTCCCCAG CTCCATCCTA
801 TCTTCCCTTC TAAGGTCTTG GAGGCTTCCC CACAAGCGAC CTACCACTGT
851 TGCGGTGCTC CAAACCTCCT CCCCACCTCC TTCTCCTCCT CCTCCCTTTC
901 CTTGGCTTTT ATCATGCTAA TATTTGCAGA AAATATTCAA TAAAGTGAGT
951 CTTTGCACTT GAAAA
```

FIG. 2

Protein translation of NPC-1 kappa light chain whole sequence.
SEQ ID NO: 2 || SEQ ID NO: 3

```
  1 AUGAGAAUACCAUUAAUUAGCUAGGGACCAAAAUUCAAAGACAAAAUGGAUUUUCAGGUG  60
                                                     MetAspPheGlnVal

61 CAGAUUUUCAGCUUCCUGCUAAUCAGUGCCUCAGUCAUACUGUCCAGAGGACAAGUUGUU 120
    GlnIlePheSerPheLeuLeuIleSerAlaSerValIleLeuSerArgGlyGlnValVal

121 CUCACCCAGUCUCCAGUAAUCAUGUCUGCAUCUCCAGGGGAGAAGGUCACCAUGACCUGC 180
    LeuThrGlnSerProValIleMetSerAlaSerProGlyGluLysValThrMetThrCys

181 AGUGCCAGCUCAAGUAUAAGUUACAUGUACUGGUACCAGCAGAAGCCAGGCACCUCCCCC 240
    SerAlaSerSerSerIleSerTyrMetTyrTrpTyrGlnGlnLysProGlyThrSerPro

241 AAAAGAUGGAUUUAUGACACAUCCAAACUGGCUUCUGGAGUCCCUGCUCGCUUCAGUGGC 300
    LysArgTrpIleTyrAspThrSerLysLeuAlaSerGlyValProAlaArgPheSerGly

301 AGUGGGUCUGGGACCUCUUAUUCUCUCACAAUCAGCAACAUGGAGGCUGGAGAUGCUGCC 360
    SerGlySerGlyThrSerTyrSerLeuThrIleSerAsnMetGluAlaGlyAspAlaAla

361 ACUUAUUACUGCCAUCAGCGGGAUUCUUACCCAUGGACGUUCGGUGGAGGCACCAACCUG 420
    ThrTyrTyrCysHisGlnArgAspSerTyrProTrpThrPheGlyGlyGlyThrAsnLeu

421 GAAAUCAAACGGGCUGAUGCUGCACCAACUGUAUCCAUCUUCCCACCAUCCAGUGAGCAG 480
    GluIleLysArgAlaAspAlaAlaProThrValSerIlePheProProSerSerGluGln

481 UUAACAUCUGGAGGUGCCUCAGUCGUGUGCUUCUUGAACAACUUCUACCCCAAAGACAUC 540
    LeuThrSerGlyGlyAlaSerValValCysPheLeuAsnAsnPheTyrProLysAspIle

541 AAUGUCAAGUGGAAGAUUGAUGGCAGUGAACGACAAAAUGGCGUCCUGAACAGUUGGACU 600
    AsnValLysTrpLysIleAspGlySerGluArgGlnAsnGlyValLeuAsnSerTrpThr

601 GAUCAGGACAGCAAAGACAGCACCUACAGCAUGAGCAGCACCCUCACGUUGACCAAGGAC 660
    AspGlnAspSerLysAspSerThrTyrSerMetSerSerThrLeuThrLeuThrLysAsp

661 GAGUAUGAACGACAUAACAGCUAUACCUGUGAGGCCACUCACAAGACAUCAACUUCACCC 720
    GluTyrGluArgHisAsnSerTyrThrCysGluAlaThrHisLysThrSerThrSerPro

721 AUUGUCAAGAGCUUCAACAGGAAUGAGUGUUAGAGACAAAGGUCCUGAGACGCCACCACC 780
    IleValLysSerPheAsnArgAsnGluCys *

781 AGCUCCCCAGCUCCAUCCUAUCUUCCCUUCUAAGGUCUUGGAGGCUUCCCCACAAGCGAC 840

841 CUACCACUGUUGCGGUGCUCCAAACCUCCUCCCCACCUCCUUCUCCUCCUCCUCCCUUUC 900

901 CUUGGCUUUUAUCAUGCUAAUAUUUGCAGAAAAUAUUCAAUAAAGUGAGUCUUUGCACUU 960

961 GAAAA 965
```

FIG. 3

NPC-1 G1 heavy chain complete sequence: translation starts at 37.
SEQ ID NO: 4

```
   1  TTTTCCATCC TCTTCTCATA GAGCCTCCAT CAGACCATGG CTGTCCTGGC
  51  ACTGCTCCTC TGCCTGGTGA CATTCCCAAG CTGTGTCCTG TCCCAGGTGC
 101  AGCTGAAGGA GTCAGGACCT GACCTGGTGG CGCCCTCACA GAGCCTGTCC
 151  ATCACATGCA CTGTCTCAGG ATTCTCATTA AGCAAATTTG GTGTAAACTG
 201  GGTTCGCCAG CCTCCAGGAA AGGGTCTGGA GTGGCTGGGA GTAATATGGG
 251  GTGACGGGAG CACAAGTTAT AATTCAGGTC TCATATCAAG ACTGAGCATC
 301  AGCAAGGAGA ACTCCAAGAG CCAGGTTTTC TTAAAACTGA ACAGTCTGCA
 351  AGCTGATGAC ACAGCCACAT ACTACTGTGT CAAACCGGGG GGTGACTACT
 401  GGGGTCACGG AACCTCAGTC ACCGTCTCCT CAGCCAAAAC GACACCCCCA
 451  TCTGTCTATC CACTGGCCCC TGGATCTGCT GCCCAAACTA ACTCCATGGT
 501  GACCCTGGGA TGCCTGGTCA AGGGCTATTT CCCTGAGCCA GTGACAGTGA
 551  CCTGGAACTC TGGATCCCTG TCCAGCGGTG TGCACACCTT CCCAGCTGTC
 601  CTGCAGTCTG ACCTCTACAC TCTGAGCAGC TCAGTGACTG TCCCCTCCAG
 651  CACCTGGCCC AGCGAGACCG TCACCTGCAA CGTTGCCCAC CCGGCCAGCA
 701  GCACCAAGGT GGACAAGAAA ATTGTGCCCA GGGATTGTGG TTGTAAGCCT
 751  TGCATATGTA CAGTCCCAGA AGTATCATCT GTCTTCATCT TCCCCCCAAA
 801  GCCCAAGGAT GTGCTCACCA TTACTCTGAC TCCTAAGGTC ACGTGTGTTG
 851  TGGTAGACAT CAGCAAGGAT GATCCCGAGG TCCAGTTCAG CTGGTTTGTA
 901  GATGATGTGG AGGTGCACAC AGCTCAGACG CAACCCCGGG AGGAGCAGTT
 951  CAACAGCACT TTCCGCTCAG TCAGTGAACT TCCCATCATG CACCAGGACT
1001  GGCTCAATGG CAAGGAGTTC AAATGCAGGG TCAACAGTGC AGCTTTCCCT
1051  GCCCCCATCG AGAAAACCAT CTCCAAAACC AAAGGCAGAC CGAAGGCTCC
1101  ACAGGTGTAC ACCATTCCAC CTCCCAAGGA GCAGATGGCC AAGGATAAAG
1151  TCAGTCTGAC CTGCATGATA ACAGACTTCT TCCCTGAAGA CATTACTGTG
```

FIG. 4A

```
1201  GAGTGGCAGT GGAATGGGCA GCCAGCGGAG AACTACAAGA ACACTCAGCC

1251  CATCATGGAC ACAGATGGCT CTTACTTCGT CTACAGCAAG CTCAATGTGC

1301  AGAAGAGCAA CTGGGAGGCA GGAAATACTT TCACCTGCTC TGTGTTACAT

1351  GAGGGCCTGC ACAACCACCA TACTGAGAAG AGCCTCTCCC ACTCTCCTGG

1401  TAAATGATCC CAGTGTCCTT GGAGCCCTCT GGTCCTACAG GACTCTGACA

1451  CCTACCTCCA CCCCTCCCTG TATAAATAAA GCACCCAGCA CTGCCTTGGG

1501  ACCCTGCAAA AAAAAAAAAA AAA
```

FIG. 4B

Protein translation of NPC-1 G1 heavy chain complete sequence.
SEQ ID NO: 5 || SEQ ID NO: 6

```
  1 UUUUCCAUCCUCUUCUCAUAGAGCCUCCAUCAGACCAUGGCUGUCCUGGCACUGCUCCUC  60
                                        MetAlaValLeuAlaLeuLeuLeu

61 UGCCUGGUGACAUUCCCAAGCUGUGUCCUGUCCCAGGUGCAGCUGAAGGAGUCAGGACCU 120
    CysLeuValThrPheProSerCysValLeuSerGlnValGlnLeuLysGluSerGlyPro

121 GACCUGGUGGCGCCCUCACAGAGCCUGUCCAUCACAUGCACUGUCUCAGGAUUCUCAUUA 180
    AspLeuValAlaProSerGlnSerLeuSerIleThrCysThrValSerGlyPheSerLeu

181 AGCAAAUUUGGUGUAAACUGGGUUCGCCAGCCUCCAGGAAAGGGUCUGGAGUGGCUGGGA 240
    SerLysPheGlyValAsnTrpValArgGlnProProGlyLysGlyLeuGluTrpLeuGly

241 GUAAUAUGGGGUGACGGGAGCACAAGUUAUAAUUCAGGUCUCAUAUCAAGACUGAGCAUC 300
    ValIleTrpGlyAspGlySerThrSerTyrAsnSerGlyLeuIleSerArgLeuSerIle

301 AGCAAGGAGAACUCCAAGAGCCAGGUUUUCUUAAAACUGAACAGUCUGCAAGCUGAUGAC 360
    SerLysGluAsnSerLysSerGlnValPheLeuLysLeuAsnSerLeuGlnAlaAspAsp

361 ACAGCCACAUACUACUGUGUCAAACCGGGGGGUGACUACUGGGGUCACGGAACCUCAGUC 420
    ThrAlaThrTyrTyrCysValLysProGlyGlyAspTyrTrpGlyHisGlyThrSerVal

421 ACCGUCUCCUCAGCCAAAACGACACCCCCAUCUGUCUAUCCACUGGCCCCUGGAUCUGCU 480
    ThrValSerSerAlaLysThrThrProProSerValTyrProLeuAlaProGlySerAla

481 GCCCAAACUAACUCCAUGGUGACCCUGGGAUGCCUGGUCAAGGGCUAUUUCCCUGAGCCA 540
    AlaGlnThrAsnSerMetValThrLeuGlyCysLeuValLysGlyTyrPheProGluPro

541 GUGACAGUGACCUGGAACUCUGGAUCCCUGUCCAGCGGUGUGCACACCUUCCCAGCUGUC 600
    ValThrValThrTrpAsnSerGlySerLeuSerSerGlyValHisThrPheProAlaVal

601 CUGCAGUCUGACCUCUACACUCUGAGCAGCUCAGUGACUGUCCCCUCCAGCACCUGGCCC 660
    LeuGlnSerAspLeuTyrThrLeuSerSerSerValThrValProSerSerThrTrpPro

661 AGCGAGACCGUCACCUGCAACGUUGCCCACCCGGCCAGCAGCACCAAGGUGGACAAGAAA 720
    SerGluThrValThrCysAsnValAlaHisProAlaSerSerThrLysValAspLysLys

721 AUUGUGCCCAGGGAUUGUGGUUGUAAGCCUUGCAUAUGUACAGUCCCAGAAGUAUCAUCU 780
    IleValProArgAspCysGlyCysLysProCysIleCysThrValProGluValSerSer

781 GUCUUCAUCUUCCCCCCAAAGCCCAAGGAUGUGCUCACCAUUACUCUGACUCCUAAGGUC 840
    ValPheIlePheProProLysProLysAspValLeuThrIleThrLeuThrProLysVal

841 ACGUGUGUUGUGGUAGACAUCAGCAAGGAUGAUCCCGAGGUCCAGUUCAGCUGGUUUGUA 900
    ThrCysValValValAspIleSerLysAspAspProGluValGlnPheSerTrpPheVal

901 GAUGAUGUGGAGGUGCACACAGCUCAGACGCAACCCCGGGAGGAGCAGUUCAACAGCACU 960
    AspAspValGluValHisThrAlaGlnThrGlnProArgGluGluGlnPheAsnSerThr
```

FIG. 5A

961  UUCCGCUCAGUCAGUGAACUUCCCAUCAUGCACCAGGACUGGCUCAAUGGCAAGGAGUUC 1020
     PheArgSerValSerGluLeuProIleMetHisGlnAspTrpLeuAsnGlyLysGluPhe

1021 AAAUGCAGGGUCAACAGUGCAGCUUUCCCUGCCCCAUCGAGAAAACCAUCUCCAAAACC 1080
     LysCysArgValAsnSerAlaAlaPheProAlaProIleGluLysThrIleSerLysThr

1081 AAAGGCAGACCGAAGGCUCCACAGGUGUACACCAUUCCACCUCCCAAGGAGCAGAUGGCC 1140
     LysGlyArgProLysAlaProGlnValTyrThrIleProProProLysGluGlnMetAla

1141 AAGGAUAAAGUCAGUCUGACCUGCAUGAUAACAGACUUCUUCCCUGAAGACAUUACUGUG 1200
     LysAspLysValSerLeuThrCysMetIleThrAspPhePheProGluAspIleThrVal

1201 GAGUGGCAGUGGAAUGGGCAGCCAGCGGAGAACUACAAGAACACUCAGCCCAUCAUGGAC 1260
     GluTrpGlnTrpAsnGlyGlnProAlaGluAsnTyrLysAsnThrGlnProIleMetAsp

1261 ACAGAUGGCUCUUACUUCGUCUACAGCAAGCUCAAUGUGCAGAAGAGCAACUGGGAGGCA 1320
     ThrAspGlySerTyrPheValTyrSerLysLeuAsnValGlnLysSerAsnTrpGluAla

1321 GGAAAUACUUUCACCUGCUCUGUGUUACAUGAGGGCCUGCACAACCACCAUACUGAGAAG 1380
     GlyAsnThrPheThrCysSerValLeuHisGluGlyLeuHisAsnHisHisThrGluLys

1381 AGCCUCUCCCACUCUCCUGGUAAAUGAUCCCAGUGUCCUUGGAGCCCUCUGGUCCUACAG 1440
     SerLeuSerHisSerProGlyLys *

1441 GACUCUGACACCUACCUCCACCCCUCCCUGUAUAAAUAAAGCACCCAGCACUGCCUUGGG 1500

1501 ACCCUGCAAAAAAAAAAAAAAAA 1523

FIG. 5B

NPC-1 Kappa chain (leader peptide, V-region, C-region, CDR regions in bold):

SEQ ID NO: 3

MDFQVQIFSFLLISASVILSRGQVVLTQSPVIMSA

Leader peptide (-22 to -1)

SPGEKVTMTCSASSSISYMYWYQQKPGTSPKRWIYDTSKLASGVPARFSG

V-region   CDR1(24 to 33)            CDR2(49 to 55)

SGSGTSYSLTISNMEAGDAATYYCHQRDSYPWTFGGGTNLEIKRADAAPT

CDR3(88 to 96)

VSIFPPSSEQLTSGGASVVCFLNNFYPKDINVKWKIDGSERQNGVLNSWT

C-region (from 109)

DQDSKDSTYSMSSTLTLTKDEYERHNSYTCEATHKTSTSPIVKSFNRNEC

FIG. 6

NPC-1 G1 chain (leader peptide, V-region, C-region, CDR regions in bold):

SEQ ID NO: 6

MAVLALLLCLVTFPSCVLSQVQLKESGPDLVAPSQSLSITCTVSGFSL
Leader peptide (-19 to -1)        V-region SKPGVNWVRQPPGKGLEWLGVIWGDGSTSYNSGLISRLSISKENSKSQVFLK
CDR1 (30-35)        CDR2 (50-65)

LNSLQADDTATYYCVKPGGDYWGHGTSVTVSSAKTTPPSVYPLAPGSAAQ
            CDR3 (95-102)        C-region (from 119)

TNSMVTLGCLVKGYFPEPVTVTWNSGSLSSGVHTFPAVLQSDLYTLSSSV

TVPSSTWPSETVTCNVAHPASSTKVDKKIVPRDCGCKPCICTVPEVSSVF

IFPPKPKDVLTITLTPKVTCVVVDISKDDPEVQFSWFVDDVEVHTAQTQP

REEQFNSTFRSVSELPIMHQDWLNGKEFKCRVKVXLSCPIEKTISKPKAD

FIG. 7

RECOMBINANT MONOCLONAL ANTIBODIES AND CORRESPONDING ANTIGENS FOR COLON AND PANCREATIC CANCERS

RELATED APPLICATION

The present application is a Divisional Application of U.S. patent application Ser. No. 13/012,679 filed Jan. 24, 2011, which is a Divisional Application of U.S. patent application Ser. No. 12/825,022 filed Jun. 28, 2010, now U.S. Pat. No. 8,535,667, which is a Continuation Application of U.S. patent application Ser. No. 12/000,701, filed Dec. 17, 2007, now U.S. Pat. No. 7,763,720, which is a Divisional of U.S. patent application Ser. No. 11/404,566, filed Apr. 14, 2006, now U.S. Pat. No. 7,314,622, which is related to, and claims benefit under 35 U.S.C. §119(e), of U.S. Provisional Patent Application No. 60/671,481, entitled "Recombinant monoclonal antibodies and corresponding antigens for colon and pancreatic cancers," filed 15 Apr. 2005, each of which is incorporated entirely herein by reference.

SEQUENCE LISTING DISCLOSURE

The biological sequence listing in the file named "43282o1006.txt" having a size of 14,766 bytes that was created Aug. 25, 2015 is hereby incorporated by reference in its entirety.

FIELD OF THE INVENTION

The present invention relates to the field of recombinant monoclonal antibodies and peptides and their uses in clinical and scientific procedures, including diagnostic procedures, especially where such processes involve the detection of human colorectal and pancreatic carcinoma-associated antigens (CPAA), and the characterization of the epitopes recognized by said recombinant monoclonal antibodies and peptides. The present invention also provides anti-CPAA antibodies and peptides in the form of diagnostic compounds and/or pharmaceutical compositions, useful for the diagnostic and/or therapeutic methods of the present invention for diagnosing and/or treating colorectal and pancreatic carcinoma-associated pathologies.

BACKGROUND OF THE INVENTION

According to the most recent data from the World Health Organization, ten million people around the world were diagnosed with the cancer in 2000, and six million died from it. Moreover, statistics indicate that the cancer incidence rate is on the rise around the globe. In America, for example, projections suggest that forty percent of those alive today will be diagnosed with some form of cancer at some point in their lives. By 2010, that number will have climbed to fifty percent. Of all cancers, colorectal cancer is the second leading cause of cancer-related deaths in the U.S., while pancreatic cancer is the eleventh most common cancer and the fourth leading cause of cancer death in both men and women. This grim scenario shows the great need for new cancer diagnostics and therapies.

Modern technology, such as that involving the use of hybridomas, has made available to researchers and clinicians sources of highly specific and potent monoclonal antibodies useful in general diagnostic and clinical procedures. For example, there are now therapeutic antibodies for the treatment of cancer, such as HERCEPTIN® (trastuzumab, Genentech) for metastatic breast cancer and PANOREX® (endrecolomab, Centocor/GlaxoSmithKline) approved in Germany for the treatment of colorectal cancer.

Yet the most important challenge in fighting cancer, according to Dr. Leland Hartwell, Nobel Laureate and Director of the Fred Hutchinson Cancer Research Center, remains the pursuit of early diagnosis. The Economist (Oct. 4, 2004). The more advanced a cancer is when diagnosed, the less likely it is that therapy will be effective.

Hence, despite the advances in cancer research, there remains a need, for recombinant monoclonal antibodies useful for the early diagnosis and treatment of colon and pancreatic carcinomas.

SUMMARY OF THE INVENTION

An object of the present invention provides for recombinant monoclonal antibodies, or portions of recombinant monoclonal antibodies (peptides) having specificity directed to antigens and epitopes of human colorectal and pancreatic carcinoma-associated antigens (CPAA). It is therefore an object of the present invention to provide for a recombinant monoclonal antibody or a portion thereof having specificity for CPAA proteins and peptides.

A further object of the present invention provides for oligonucleotides, such as cDNAs, whose nucleotide sequences (genes) encode part or all of the heavy and light chains of the aforementioned recombinant antibodies. Accordingly, an aspect of the present invention provides for a gene encoding the variable region of a monoclonal antibody, specifically recognizing CPAA, especially determinants or epitopes that commonly exist in all CPAA.

A further object of the present invention provides for a recombinant vector comprising the above genes. A further object of the present invention provides for a transformant obtained using the above recombinant vector.

It is a still further object of the present invention to provide recombinant antibodies specific for CPAA, wherein said antibodies are tagged with markers, making them easily isolatable as well as affording versatility in using said antibodies for research, diagnostic and clinical purposes. A further aspect of the invention provides for a chimeric antibody that includes the variable regions of the heavy and light chains of CPAA-specific murine antibody linked to the human immunoglobulin gamma-1 and kappa constant regions, respectively.

It is another object of the present invention to provide a method of using the recombinant antibodies disclosed herein for research, diagnostic, and clinical uses. Particularly, an object of the present invention provides a diagnostic tool for the early detection of cancers, perhaps in patients without symptoms of disease. Another aspect provides for an immunohistochemical tool for distinguishing between slow and aggressive pancreatic cancers.

Another object of the invention provides a method for promoting tumor regression or triggering the death of transformed cells comprising administering to a patient in need thereof an antibody, portion, fragment, peptide or derivative thereof that binds to a CPAA antigen, wherein a said antibody is administered in sufficient amounts to promote tumor regression or cell death.

Yet another object of the present invention provides for methods having utility for in vitro, in situ and/or in vivo diagnosis and/or treatment of animal cells, tissues or pathologies associated with the presence of CPAA, using anti-CPAA antibodies and/or anti-CPAA peptides. The present invention also provides anti-CPAA antibodies and peptides in the form of pharmaceutical and/or diagnostic compounds and/or compositions, useful for the diagnostic and/or therapeutic methods of the present invention for diagnosing and/or treating CPAA-related pathologies.

The present invention is also directed to an anti-CPAA chimeric antibody comprising two light chains and two heavy chains, each of the chains comprising at least part of a human constant region and at least part of a variable (V) region of non-human origin having specificity to CPAA, said antibody binding with high affinity and/or high avidity to an inhibiting and/or neutralizing epitope of CPAA-associated cells. The invention also includes a fragment or a derivative such an antibody, such as one or more portions of the antibody chain, such as the heavy chain constant, joining, diversity or variable regions, or the light chain constant, joining or variable regions.

It is a further object of the invention to identify the specific epitopes associated with the CPAA peptides identified by the monoclonal antibodies or portions thereof. Such antigenic sequences may be useful in generating additional antigen-binding ligands, or be used as vaccines or other immunostimulatory means.

Methods are also provided for making and using anti-CPAA antibodies and peptides for various utilities of the present invention, such as but not limited to, hybridoma, recombinant or chemical synthetic methods for producing anti-CPAA antibodies or anti-CPAA peptides according to the present invention; detecting CPAA in a solution or cell; inhibiting one or more biological activities of CPAA-bearing cells in vitro, in situ or in vivo, including killing such CPAA-bearing cells. Hence, such inhibition and killing can include treatment methods of the present invention for alleviating symptoms or pathologies involving CPAA-bearing cells, such as malignancies.

BRIEF DESCRIPTION OF THE SEVERAL VIEWS OF THE DRAWINGS

FIG. 1 is a tracing showing an HPLC elution profile of the Hollinshead "vaccine", a partially purified preparation of colorectal and pancreatic carcinoma cell membranes.

FIG. 2 presents the entire cDNA sequence (SEQ ID NO:1) of the NPC-1 kappa light chain.

FIG. 3 depicts the nucleic acid sequence (SEQ ID NO:2) and corresponding amino acid sequence (SEQ ID NO:3) of the NPC-1 kappa light chain.

FIGS. 4A-B presents the entire cDNA sequence (SEQ ID NO:4) of NPC-1 heavy chain.

FIGS. 5A-B depicts the nucleic acid sequence (SEQ ID NO:5) and corresponding amino acid sequence (SEQ ID NO:6) of the NPC-1 heavy chain.

FIG. 6 depicts the CDR 1 (SEQ ID NO:7), CDR 2 (SEQ ID NO:8), and CDR 3 (SEQ ID NO:9) of NPC-1 in the Light Chain Sequence.

FIG. 7 identifies the CDR 1 (SEQ ID NO:10), CDR 2 (SEQ ID NO:11), and CDR 3 (SEQ IN NO:12) of NPC-1 in the Heavy Chain Sequence.

DETAILED DESCRIPTION OF THE INVENTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. Thus, for example, the reference to an antibody is a reference to one or more such antibodies, including equivalents thereof known to those skilled in the art. Other than in the operating examples, or where otherwise indicated, all numbers expressing quantities of ingredients or reaction conditions used herein should be understood as modified in all instances by the term "about." The term "about" when used in connection with percentages may mean±1%.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described here.

The present invention provides for recombinant monoclonal antibodies and peptides and their uses in clinical and scientific procedures, including diagnostic procedures, especially where such processes involve the detection of human colorectal and pancreatic carcinoma-associated antigens (CPAA), and the characterization of the epitopes recognized by said recombinant monoclonal antibodies and peptides. The present invention also provides anti-CPAA antibodies and peptides in the form of diagnostic compounds and/or pharmaceutical compositions, useful for the diagnostic and/or therapeutic methods of the present invention for diagnosing and/or treating colorectal and pancreatic carcinoma-associated pathologies.

Generally, monoclonal antibodies are used as invaluable reagents in diagnostics. In fact, they have played a major role in deciphering the functions of various bio-molecules in cryptic biosynthetic pathways. These have also become the reagents of choice for identification and characterization of tumor specific antigens and have become a valuable tool in the classification of cancer.

With the advent of methods of molecular biology and recombinant technology, it is now possible to produce antibody molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric ($H_2 L_2$) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3 dimensional structure. This structure is often given as $H_2 L_2$ and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contain the amino acid sequences capable of specifically binding to antigenic targets.

As used herein, the term "antigen binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues.

Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The accepted CDR regions have been described by Kabat et al, 252 J. Biol. Chem. 6609-16 (1977), and CDR loops may be identified by applying these rules during an examination of a linear amino acid sequence. The rules for defining the CDR-H3 loop can vary, however (see Chapter 4, Antibody Engineering: Methods & Protocols, (Lo, ed. Humana Press, Totowa, N.J., 2004)), and the actual boundaries of some CDR-H3 loops may not be identified without experimental techniques such as circular dichroism, nuclear magnetic resonance, or X-ray crystallography.

In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

Regarding the antigenic determinate recognized by the CDR regions of the antibody, this is also referred to as the "epitope." In other words, epitope refers to that portion of any molecule capable of being recognized by, and bound by, an antibody (the corresponding antibody binding region may be referred to as a paratope). In general, epitopes consist of chemically active surface groupings of molecules, for example, amino acids or sugar side chains, and have specific three-dimensional structural characteristics as well as specific charge characteristics.

An "antigen" is a molecule or a portion of a molecule capable of being bound by an antibody which is additionally capable of inducing an animal to produce an antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

Thus, the term "antibody" is meant to include both intact immunoglobulin molecules as well as portions, fragments, peptides and derivatives thereof, such as, for example, Fab, Fab', $F(ab')_2$, Fv, CDR regions, or any portion or peptide sequence of the antibody that is capable of binding antigen or epitope. An antibody is said to be "capable of binding" a molecule if it is capable of specifically reacting with the molecule to thereby bind the molecule to the antibody.

Antibody also includes chimeric antibodies, anti-idiotypic (anti-Id) antibodies to antibodies that can be labeled in soluble or bound form, as well as fragments, portions, regions, peptides or derivatives thereof, provided by any known technique, such as, but not limited to, enzymatic cleavage, peptide synthesis, or recombinant techniques. Such antibodies of the present invention are capable of binding portions of CPAA or CPAA-bearing cells. Antibody fragments or portions may lack the Fc fragment of intact antibody, clear more rapidly from the circulation, and may have less non-specific tissue binding than an intact antibody. Examples of antibody may be produced from intact antibodies using methods well known in the art, for example by proteolytic cleavage with enzymes such as papain (to produce Fab fragments) or pepsin (to produce $F(ab')_2$ fragments). See e.g., Wahl et al., 24 J. Nucl. Med. 316-25 (1983). Portions of antibodies may be made by any of the above methods, or may be made by expressing a portion of the recombinant molecule. For example, the CDR region(s) of a recombinant antibody may be isolated and subcloned into the appropriate expression vector. See, e.g., U.S. Pat. No. 6,680,053.

NPC-1 Oligonucleotide and Amino Acid Sequences

The present invention includes, within its scope, DNA sequences encoding the variable regions of the light and heavy chains of the anti-CPAA antibody of the present invention. A nucleic acid sequence encoding the variable region of the light chain of NPC-1 is presented in FIG. 2 (SEQ ID NO:1). A nucleic acid sequence encoding the variable region of the heavy chain of NPC-1 is presented in FIG. 4 (SEQ ID NO:4).

The present invention includes, within its scope, an amino acid sequence of the NPC-1 light chain comprising the peptides depicted in FIG. 3 (SEQ ID NO:3), and an amino acid sequence of the NPC-1 heavy chain comprising the peptides of FIG. 5 (SEQ ID NO:6). Further, the present invention includes the CDR regions depicted for the kappa light chain in FIG. 6, which include the amino acid sequences for CDR1 (SEQ ID NO:7): SASSSISYMY; CDR2 (SEQ ID NO:8): DTSKLAS; and CDR3 (SEQ ID NO:9): HQRDSYPWT. The invention similarly identifies the CDR regions for the heavy chain in FIG. 7, which include the amino acid sequences for CDR 1 (SEQ ID NO:10): SKFGVN (SEQ ID NO:10); CDR 2 (SEQ ID NO:11): VIWGDGSTSYNSGLIS; and CDR3: (SEQ ID NO:12) CVKPGGDY.

Included also within the scope of the invention is any oligonucleotide sequence that encodes the amino acid sequence of NPC-1 or a peptide thereof. Because the genetic code is degenerate, more than one codon can be used to encode a particular amino acid. Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-CPAA antibody or portion. Such "codon usage rules" are disclosed by Lathe, et al., 183 J. Molec. Biol. 1-12 (1985). Using the "codon usage rules" of Lathe, a single oligonucleotide, or a set of oligonucleotides, that contains a theoretical "most probable" nucleotide sequence capable of encoding anti-CPAA sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding an anti-CPAA antibody or peptide including a variable or constant region is used to identify the sequence of a complementary oligonucleotide or set of oligo-nucleotides which is capable of hybridizing to the "most probable" sequence, or set of sequences. An oligonucleotide containing such a complementary sequence can be employed as a probe to identify and isolate the variable or constant region anti-CPAA gene (Sambrook et al., 1989).

A suitable oligonucleotide, or set of oligonucleotides, which is capable of encoding a peptide of NPC-1 (or which is complementary to such an oligonucleotide, or set of oligonucleotides) is identified (using the above-described procedure), synthesized, and hybridized by means well known in the art, against a DNA or a cDNA preparation derived from cells which are capable of expressing anti-CPAA antibodies or variable or constant regions thereof. Single stranded oligonucleotide molecules complementary to the "most probable" anti-CPAA region peptide coding sequences can be synthesized using procedures which are well known to those of ordinary skill in the art. See Belagaje et al., 254 J. Biol. Chem. 5765-80 (1979); Maniatis et al., in Molecular Mechanisms in the Control of Gene Expression (Nierlich, et al., eds., Acad. Press, N.Y., 1976); Wu et al., 1978; Khorana, 203 Science 614-25 (1979).

Additionally, DNA synthesis can be achieved through the use of automated synthesizers. Techniques of nucleic acid hybridization are disclosed by Sambrook et al., 1989, and by Hayrnes et al., in Nucleic Acid Hybridization, A Practical Approach (IRL Press, D.C. 1985). Hybridization wash conditions can include wash solution of 0.2.times.SSC/0.1% SDS and incubation with rotation for 10 minutes at room temperature, (low stringency wash), wash solution of prewarmed (42° C.) 0.2×SSC/0.1% SDS and incubation with rotation for fifteen minutes at 42° C. (medium stringency wash) and wash solution of prewarmed (68° C.) 0.1.times.SSC/0.1% SDS and incubation with rotation for fifteen minutes at 68° C. (high stringency wash). See Ausubel et al., Antibodies: a Laboratory Manual, (Harlow & Lane eds., Cold Spring Harbor Lab., 1988). Techniques such as, or similar to, those described above have successfully enabled the cloning of genes for human aldehyde dehydrogenases (Hsu et al., 82 Proc. Natl. Acad. Sci. USA 3771-75 (1985)), fibronectin (Suzuki et al., 4 Bur. Mol. Biol. Organ. J. 2519-24 (1985)), the human estrogen receptor gene (Walter et al., 82 Proc. Nad. Acad. Sci. USA 7889-93 (1985)), tissue-type plasminogen activator (Pennica et al., 301 Nature 214-21 (1983)) and human term placental alkaline phosphatase complementary DNA (Keun et al., 82 Proc. Natl. Acad Sci. USA 8715-19 (1985)).

It is also intended that the antibody coding regions for use in the present invention could also be provided by altering existing antibody genes using standard molecular biological techniques that result in variants (agonists) of the antibodies and peptides described herein. Such variants include, but are not limited to deletions, additions and substitutions in the amino acid sequence of the anti-CPAA antibodies or peptides.

For example, one class of substitutions is conserved amino acid substitutions. Such substitutions are those that substitute a given amino acid in a anti-CPAA antibody peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent is found in Bowie et al., 247 Science 1306-10 (1990).

Variant or agonist anti-CPAA antibodies or peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Science 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899-904 (1992); de Vos et al., 255 Science 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties (2nd ed., T. E. Creighton, W. H. Freeman and Company, New York 1993). Many detailed reviews are available on this subject, such as by Wold, Posttranslational Covalent Modification of proteins, 1-12 (Johnson, ed., Academic Press, New York 1983); Seifter et al. 182 Meth. Enzymol. 626-46 (1990); and Rattan et al. 663 Ann. N.Y. Acad. Sci. 48-62 (1992).

Accordingly, the antibodies and peptides of the present invention also encompass derivatives or analogs in which a substituted amino acid residue is not one encoded by the genetic code, in which a substituent group is included pegylation as mentioned previously.

Similarly, the additions and substitutions in the amino acid sequence as well as variations, and modifications just described may be equally applicable to the amino acid sequence of the CPAA antigen and/or epitope or peptides thereof, and are thus encompassed by the present invention. As mentioned above, the genes encoding the monoclonal antibody according to the present invention is specifically effective in the recognition of CPAA.

Recombinant Expression of Antibodies

Traditionally, monoclonal antibodies have been produced as native molecules in murine hybridoma lines. In addition to that technology, reviewed below, the present invention provides for recombinant DNA expression of monoclonal antibodies. This allows the production of humanized antibodies as well as spectrum of antibody derivatives and fusion proteins in a host species of choice. More recently, the production of antibodies in bacteria, yeast, transgenic animals and chicken eggs have emerged as promising alternatives for hybridoma-based production systems. The main advantages of transgenic animals are potential high yields from renewable sources.

A nucleic acid sequence encoding at least one anti-CPAA antibody, portion or polypeptide of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, A Laboratory Manual, Cold Spring Harbor Lab., Cold Spring Harbor, N.Y. (1982); Sambrook et al. Molecular Cloning: A Laboratory Manual (Cold Spring Harbor Lab. Press 1989), and Ausubel, 1987, 1993, may be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-CPAA peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

The present invention accordingly encompasses the expression of an anti-CPAA antibody or peptide, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin, but any other mammalian cell may be used.

Further, by use of, for example, the yeast ubiquitin hydrolase system, in vivo synthesis of ubiquitin-transmembrane polypeptide fusion proteins may be accomplished. The fusion proteins so produced may be processed in vivo or purified and processed in vitro, allowing synthesis of an anti-CPAA antibody or polypeptide of the present invention with a specified amino terminus sequence. Moreover, problems associated with retention of initiation codon-derived methionine residues in direct yeast (or bacterial) expression maybe avoided. Sabin et al., 7(7) Bio/Technol. 705-09 (1989); Miller et al., 7(7) Bio/Technol. 698-704 (1989).

Any of a series of yeast gene expression systems incorporating promoter and termination elements from the actively expressed genes coding for glycolytic enzymes produced in large quantities when yeast are grown in mediums rich in glucose can be utilized to obtain anti-CPAA antibodies or peptides of the present invention. Known glycolytic genes can also provide very efficient transcriptional control signals. For example, the promoter and terminator signals of the phosphoglycerate kinase gene can be utilized.

Production of anti-CPAA antibodies or peptides or functional derivatives thereof in insects can be achieved, for example, by infecting the insect host with a baculovirus engineered to express a transmembrane polypeptide by methods known to those of skill See Ausubel et al., 1987, 1993.

In one embodiment, the introduced nucleotide sequence will be incorporated into a plasmid or viral vector capable of autonomous replication in the recipient host. Any of a wide variety of vectors may be employed for this purpose. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli* (such as, for example, pBR322, ColE1, pSC101, pACYC 184, πVX). Such plasmids are, for example, disclosed by Maniatis et al., 1989; Ausubel et al, 1987, 1993. *Bacillus* plasmids include pC194, pC221, pT127, etc. Such plasmids are disclosed by Gryczan, in The Molecular Biology of the Bacilli 307-329 (Academic Press, NY 1982). Suitable Streptomyces plasmids include pIJ101 (Kendall et al., 169 J. Bacteriol. 4177-83 (1987)), and streptomyces bacteriophages such as φC31 (Chater et al., in Sixth Int'l Symposium on Actinomycetales Biology 45-54 (Akademiai Kaido, Budapest, Hungary 1986). *Pseudomonas* plasmids are reviewed by John et al., 8 Rev. Infect. Dis. 693-704 (1986); Izaki, 33 Jpn. J. Bacteriol. 729-42 (1978); and Ausubel et al., 1987, 1993.

Alternatively, gene expression elements useful for the expression of cDNA encoding anti-CPAA antibodies or peptides include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 Proc. Natl. Acad. Sci., USA 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983).

Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engineering 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an anti-CPAA peptide or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In one embodiment, the fused genes encoding the anti-CPAA peptide or chimeric H and L chains, or portions thereof, are assembled in separate expression vectors that are then used to co-transfect a recipient cell.

Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes.

Examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo).

Selection of cells expressing gpt is based on the fact that the enzyme encoded by this gene utilizes xanthine as a substrate for purine nucleotide synthesis, whereas the analogous endogenous enzyme cannot. In a medium containing (1) mycophenolic acid, which blocks the conversion of inosine monophosphate to xanthine monophosphate, and (2) xanthine, only cells expressing the gpt gene can survive. The product of the neo blocks the inhibition of protein synthesis by the antibiotic G418 and other antibiotics of the neomycin class.

The two selection procedures can be used simultaneously or sequentially to select for the expression of immunoglobulin chain genes introduced on two different DNA vectors into a eukaryotic cell. It is not necessary to include different selectable markers for eukaryotic cells; an H and an L chain vector, each containing the same selectable marker can be co-transfected. After selection of the appropriately resistant cells, the majority of the clones will contain integrated copies of both H and L chain vectors and/or anti-CPAA peptides.

Alternatively, the fused genes encoding the chimeric H and L chains can be assembled on the same expression vector.

For transfection of the expression vectors and production of the chimeric antibody, the recipient cell line may be a myeloma cell. Myeloma cells can synthesize, assemble and secrete immunoglobulins encoded by transfected immunoglobulin genes and possess the mechanism for glycosylation of the immunoglobulin. For example the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a chimeric antibody construct or anti-CPAA polypeptide of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988).

Another way of introducing DNA into lymphoid cells is by electroporation. Potter et al., 81 Proc. Natl. Acad. Sci. USA 7161 (1984); Yoshikawa et al., 77 Jpn. J. Cancer Res. 1122-33 (1986). In this procedure, recipient cells are subjected to an electric pulse in the presence of the DNA to be incorporated. Typically, after transfection, cells are allowed to recover in complete medium for about 24 hours, and are then seeded in 96-well culture plates in the presence of the selective medium. G418 selection is performed using about 0.4 to 0.8 mg/ml G418. Mycophenolic acid selection utilizes about 6 μg/ml plus about 0.25 mg/ml xanthine. The electroporation technique is expected to yield transfection frequencies of about $10^{-5}$ to about $10^{-4}$ for $Sp^{2/0}$ cells. In the protoplast fusion method, lysozyme is used to strip cell walls from catarrhal harboring the recombinant plasmid containing the chimeric antibody gene. The resulting spheroplasts are fused with myeloma cells with polyethylene glycol.

The immunoglobulin genes of the present invention can also be expressed in nonlymphoid mammalian cells or in other eukaryotic cells, such as yeast, or in prokaryotic cells, in particular bacteria.

Yeast provides substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Int'l Conference on Yeast, Genetics & Molecular Biol. (Montpelier, France, 1982).

Yeast gene expression systems can be routinely evaluated for the levels of production, secretion and the stability of anti-CPAA peptides, antibody and assembled murine and chimeric antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning, 45-66, (Glover, ed., IRL Press, 1985).

Bacterial strains can also be utilized as hosts for the production of antibody molecules or peptides described by this invention, E. coli K12 strains such as E. coli W3110 (ATCC 27325), and other enterobacteria such as Salmonella typhimurium or Serratia marcescens, and various Pseudomonas species can be used.

Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine and chimeric antibodies, fragments and regions or antibody chains encoded by the cloned immunoglobulin cDNAs in bacteria (see Glover, 1985; Ausubel, 1987, 1993; Sambrook, 1989; Colligan, 1992-1996).

Host mammalian cells may be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61).

Many vector systems are available for the expression of cloned anti-CPAA peptides H and L chain genes in mammalian cells (see Glover, 1985). Different approaches can be followed to obtain complete $H_2 L_2$ antibodies. As discussed above, it is possible to co-express H and L chains in the same cells to achieve intracellular association and linkage of H and L chains into complete tetrameric $H_2 L_2$ antibodies and/or anti-CPAA peptides. The co-expression can occur by using either the same or different plasmids in the same host. Genes for both H and L chains and/or anti-CPAA peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing anti-CPAA peptides and/or $H_2 L_2$ molecules via either route could be transfected with plasmids encoding additional copies of peptides, H, L, or H plus L chains in conjunction with additional selectable markers to generate cell lines with enhanced properties, such as higher production of assembled $H_2 L_2$ antibody molecules or enhanced stability of the transfected cell lines.

Additionally, plants have emerged recently as a convenient, safe and economical alternative main-stream expression systems for recombinant antibody production, which are based on large scale culture of microbes or animal cells. Antibodies may be expressed in plant cell culture, or plants grown conventionally. The expression in plants may be systemic, limited to susb-cellular plastids, or limited to seeds (endosperms). See, e.g., U.S. Patent Appl. Pub. No. 20030167531; U.S. Pat. No. 6,080,560 and U.S. Pat. No. 6,512,162; and WO 0129242. Several plant-derived antibodies have reached advanced stages of development, including clinical trials (see, e.g., Biolex, NC).

Hybridoma Technology

The present invention provides for a hybridoma cell line that produces a monoclonal antibody that has a high degree of specificity and affinity towards CPAA. The present invention relates also to variants and mutants of the hybridoma cell lines characterised in detail above that occur spontaneously or that can be produced artificially using known methods and that still have the characteristic properties of the starting material, that is to say are still capable of producing the antibodies according to the invention or derivatives thereof and secreting them into the surrounding medium.

The present invention also includes methods for the production of said hybridoma cell lines and to methods for the production of said monoclonal antibodies. Clones and sub-clones of hybridoma cell lines are to be understood as being hybridomas that are produced from the starting clone by repeated cloning and that still have the features of the starting clone that are essential to the invention.

More specifically, nucleic acid, protein or peptide molecules of the invention may be utilized to develop monoclonal or polyclonal antibodies that bind CPAA. For preparation of the CPAA-binding antibodies of the present invention, any technique which provides for the production of antibody molecules by continuous cell lines in culture may be used. For example, the hybridoma technique originally developed by Kohler and Milstein (256 Nature 495-497 (1975)) may be used. See also U.S. Pat. No. 4,376,110; Ausubel et al., Antibodies: a Laboratory Manual, (Harlow & Lane eds., Cold Spring Harbor Lab. 1988); Current Protocols in Immunology, (Colligan et al., eds., Greene Pub. Assoc. & Wiley Interscience N.Y., 1992-1996).

Another advantageous route for creating high affinity and/or high avidity human antibodies involves antigen priming of native human splenocytes in vitro, transferral of the resultant in vitro antigen primed splenocyte cells to an immunocompromised donor, e.g., a SCID mouse, boosting the immunocompromised donor with antigen, isolating human antibody secreting B-cells (IgG secreting) from the donor, and EBV-transforming the isolated human antibody secreting cells, as described in U.S. Pat. No. 6,537,809.

Chimeric Humanized and Fully Humanized Antibodies

The antibodies of the present invention include chimeric antibodies comprising part human and part mouse antibodies, in which the constant region from human antibodies are cloned to a variable regions of light and heavy chains from mouse. In some instances, 70% of the human sequences are retained. Humanized antibodies are chimeric antibodies in which perhaps 90% of the human antibody framework is retained, and combined only with the murine the complementary determining regions. Fully humanized antibodies are also contemplated in the present invention.

Recombinant murine or chimeric murine-human or human-human antibodies that bind an epitope included in the amino acid sequences of CPAA can be provided according to the present invention using known techniques based on the teaching provided herein. See, e.g., Current Protocols in Molecular Biology (Ausubel et al., eds. Wiley Interscience, N.Y., 1987, 1992, 1993); Sambrook et al. Molecular Cloning: A Laboratory Manual (Cold Spring Harbor Lab. Press 1989). For example, an antibody may be humanized by grafting the desired CDRs onto a human framework according to EP0239400.

The DNA encoding an anti-CPAA antibody of the present invention can be genomic DNA or cDNA which encodes at least one of the heavy chain constant region ($H_c$), the heavy chain variable region ($H_v$), the light chain variable region ($L_v$) and the light chain constant regions ($L_c$). A convenient alternative to the use of chromosomal gene fragments as the source of DNA encoding the murine V region antigen-binding segment is the use of cDNA for the construction of chimeric immunoglobulin genes. See e.g., Liu et al. 84 Proc. Natl. Acad. Sci., USA 3439 (1987); 139 J. Immunology 3521 (1987). The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding murine V and C region antigen-binding segments having anti-CPAA activity can be provided using known methods based on the use of the DNA sequences presented in FIG. 2-FIG. 5 (SEQ ID NOS:1-2, 4-5). Probes that bind a portion of the DNA sequences presented in FIG. 2 (SEQ ID NO:1) or FIG. 4 (SEQ ID NO:4) can be used to isolate DNA from hybridomas expressing anti-CPAA antibodies, fragments or regions, as presented herein, according to the present invention, by known methods.

Oligonucleotides representing the CPAA-binging antibodies light and heavy chains, presented in FIG. 2-FIG. 5 (SEQ ID NOS:1-2, 4-5) useful for screening for the presence of homologous genes and for the cloning of such genes encoding variable or constant regions of an anti-CPAA antibody. Such probes usually bind to DNA sequences (cDNA, genomic DNA, or any other DNA) that encode the amino acid sequences depicted in FIG. 6 (SEQ ID NO:3) and FIG. 7 (SEQ ID NO:6) to the light chain or heavy chain CDR regions which bind an epitope of CPAA. Such techniques for synthesizing such oligonucleotides are well known. See e.g., Wu et al., 21 Prog. Nucl. Acid. Res. Molec. Biol. 101-41 (1978); Ausubel et al., 1987, 1993.

In an alternative way of cloning a polynucleotide encoding an anti-CPAA variable or constant region, a library of expression vectors is prepared by cloning DNA or cDNA (from a cell capable of expressing an anti-CPAA antibody or variable or constant region) into an expression vector. The library is then screened for members capable of expressing a protein which competitively inhibits the binding of an anti-CPAA antibody, such as A2 or cA2, and which has a nucleotide sequence that is capable of encoding peptides that have the same amino acid sequence as anti-CPAA antibodies or fragments thereof. In this embodiment, DNA, such as cDNA, is extracted and purified from a cell which is capable of expressing an anti-CPAA antibody or fragment. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). See, e.g., Ausubel, 1987, 1993; Harlow, 1988; Colligan, 1992-1996; Nyyssonen et al. 11 Bio/Technology 591-95 (1993); Marks et al., 11 Bio/Technology 1145-49 (1993).

Once nucleic acid encoding such variable or constant anti-CPAA regions is isolated, the nucleic acid can be appropriately expressed in a host cell, along with other constant or variable heavy or light chain encoding nucleic acid, in order to provide recombinant monoclonal antibodies that bind CPAA with inhibitory activity. Such antibodies may include a murine or human anti-CPAA variable region which contains a framework residue having complementarity determining residues which are responsible for antigen binding. In one embodiment, an anti-CPAA variable light or heavy chain encoded by a nucleic acid as described above binds an epitope of at least five amino acids. The amino acid sequences of such anti-CPAA variable light or heavy chains are depicted in FIG. 6 (SEQ ID NO:3) and FIG. 7 (SEQ ID NO:6).

Human genes which encode the constant (C) regions of the murine and chimeric antibodies, fragments and regions of the present invention can be derived from a human fetal liver library, by known methods. Human C regions genes can be derived from any human cell including those which express and produce human immunoglobulins. The human $C_H$ region can be derived from any of the known classes or isotypes of human H chains, including γ, μ, α, δ or ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). For example, the $C_H$ region is derived from gamma 1 (IgG1), gamma 3 (IgG3), gamma 4 (IgG4), or μ (IgM). The human $C_L$ region can be derived from either human L chain isotype, kappa or lambda.

Genes encoding human immunoglobulin C regions are obtained from human cells by standard cloning techniques (Sambrook et al., 1989; Ausubel et al., 1987, 1993). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the $CH_1$ domain and hinge region of the H chain, followed by a translational stop codon to yield the truncated molecule.

Generally, the murine, human or murine and chimeric antibodies, fragments and regions of the present invention are produced by cloning DNA segments encoding the H and L chain antigen-binding regions of a CPAA-specific antibody, and joining these DNA segments to DNA segments encoding $C_H$ and $C_L$ regions, respectively, to produce murine, human or chimeric immunoglobulin-encoding genes.

Thus, in one embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions, the method of producing the chimeric antibody according to the present invention involves several steps, outlined below:

1. isolation of messenger RNA (mRNA) from the cell line producing an anti-CPAA antibody and from optional additional antibodies supplying heavy and light constant regions; cloning and cDNA production therefrom;

2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody;

3. Construction of complete H or L chain coding sequences by linkage of the cloned specific V region gene segments to cloned C region gene, as described above;

4. Expression and production of L and H chains in selected hosts, including prokaryotic and eukaryotic cells to provide murine-murine, human-murine, human-human or human murine antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C ($C_k$) region and the complete human gamma-1 C region ($C_{\gamma-1}$). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human $C_{\gamma-1}$ region can be modified by introducing a termination codon thereby generating a gene sequence which encodes the H chain portion of a Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Among these are vehicles carrying a functionally complete human $C_H$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C region; polyadenylation and transcription termination occur at native chromosomal sites downstream of the human coding regions. See U.S. Pat. No. 6,835,823.

"Fully humanized antibodies" against CPAA are also contemplated in the present invention. Fully humanized antibodies are molecules containing both the variable and constant region of the human immunoglobulin. Fully humanized antibodies can be potentially used for therapeutic use, where repeated treatments are required for chronic and relapsing diseases such as autoimmune diseases. One method for the preparation of fully human antibodies consist of "humanization" of the mouse humoral immune system, i.e. production of mouse strains able to produce human Ig (Xenomice), by the introduction of human immunoglobulin (Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunization with antigen. Fully humanized antibodies and methods for their production are known in the art. See, e.g., U.S. Pat. No. 6,835,823.

An aspect of the present invention provides for the production of a humanized antibody, which is prepared according to the invention by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors may be the same vector. The invention further provides: a DNA sequence encoding the light chain or the heavy chain of the humanized antibody; an expression vector which incorporates a said DNA sequence; and a host transformed with a said expression vector.

Generating a humanized antibody from the sequences provided herein can be practiced by those of ordinary skill in the art without undue experimentation. There are four general steps to humanize a monoclonal antibody, see, e.g., U.S. Pat. No. 5,585,089; U.S. Pat. No. 6,835,823; and U.S. Pat. No. 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Regarding the nucleotide and predicted amino acid sequences, there are two general methods for cloning a given antibody's heavy and light chain variable domain cDNAs: (a) via a conventional cDNA library, or (b) via the polymerase chain reaction (PCR). Both of these methods are widely known, see, e.g., U.S. Patent Appl. Pub. No. 2003/0166871. Given the nucleotide sequence of the cDNAs, it is a simple matter to translate this information into the predicted amino acid sequence of the antibody variable domains. In the present instance, the nucleotide sequence and predicted amino acid sequence of the light and heavy chains of the NPC-1 antibody are shown in FIG. 2 (SEQ ID NOS:2-3) and FIG. 5 (SEQ ID NOS:5-6), respectively.

Regarding the design of the humanized antibody, there are several factors to consider in deciding which human antibody sequence to use during the humanization. The humanization of light and heavy chains are considered independently of one another, but the reasoning is basically similar for each. This selection process is based on the following rationale: A given antibody's antigen specificity and affinity is primarily determined by the amino acid sequence of the variable region CDRs. Variable domain framework residues have little or no direct contribution. The primary function of the framework regions is to hold the CDRs in their proper spatial orientation to recognize antigen. Thus, the substitution of rodent CDRs such as those presented in FIG. 6 and SEQ ID NOS:7-9 or FIG. 7 and (SEQ ID NOS:10-12), into a human variable domain framework is most likely to result in retention of their correct spatial orientation if the human variable domain framework is highly homologous to the rodent variable domain from which they originated. A human variable domain should be chosen, therefore, that is highly homologous to the rodent variable domain(s).

A suitable human antibody variable domain sequence can be selected as follows:

1. Using a computer program, search all available protein (and DNA) databases for those human antibody variable domain sequences that are most homologous to the rodent antibody variable domains. The output of a suitable program is a list of sequences most homologous to the rodent antibody, the percent homology to each sequence, and an alignment of each sequence to the rodent sequence. This is done independently for both the heavy and light chain variable domain sequences. The above analyses are more easily accomplished if only human immunoglobulin sequences are included.

2. List the human antibody variable domain sequences and compare for homology. Primarily, the comparison is performed on length of CDRs, except CDR3 of the heavy chain which is quite variable. Human heavy chains and Kappa and Lambda light chains are divided into subgroups; Heavy chain 3 subgroups, Kappa chain 4 subgroups, Lambda chain 6 subgroups. The CDR sizes within each subgroup are similar but vary between subgroups. It is usually possible to match a rodent antibody CDR to one of the human subgroups as a first approximation of homology. Antibodies bearing CDRs of similar length are then compared for amino acid sequence homology, especially within the CDRs, but also in the surrounding framework regions. The human variable domain which is most homologous is chosen as the framework for humanization.

The actual humanizing methodologies and techniques are also within the grasp of those of ordinary skill in the art. A DNA sequence encoding the desired reshaped antibody can therefore be made beginning with the human DNA whose CDRs it is wished to reshape. The rodent variable domain amino acid sequence containing the desired CDRs is compared to that of the chosen human antibody variable domain sequence. The residues in the human variable domain are marked that need to be changed to the corresponding residue in the rodent to make the human variable region incorporate the rodent CDRs. There may also be residues that need substituting in, adding to or deleting from the human sequence.

Oligonucleotides are synthesized that can be used to mutagenize the human variable domain framework to contain the desired residues. Those oligonucleotides can be of any convenient size. One is normally only limited in length by the capabilities of the particular synthesizer one has available. The method of oligonucleotide-directed in vitro mutagenesis is well known.

Alternatively, humanization may be achieved using the recombinant polymerase chain reaction (PCR) methodology of U.S. Pat. No. 5,858,725. Using this methodology, a CDR may be spliced between the framework regions of a human antibody. In general, the technique of U.S. Pat. No. 5,858,725 can be performed using a template comprising two human framework regions, AB and CD, and between them, the CDR which is to be replaced by a donor CDR. Primers A and B are used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanized product in a single reaction.

Following the mutagenesis reactions to reshape the antibody, the mutagenized DNAs can be linked to an appropriate DNA encoding a light or heavy chain constant region, cloned into an expression vector, and transfected into host cells, such as mammalian cells. These steps can be carried out in routine fashion. A reshaped antibody may therefore be prepared by a process comprising:

(a) preparing a first replicable expression vector including a suitable promoter operably linked to a DNA sequence which encodes at least a variable domain of an Ig heavy or light chain, the variable domain comprising framework regions from a human antibody and the CDRs required for the humanized antibody of the invention;

(b) preparing a second replicable expression vector including a suitable promoter operably linked to a DNA sequence which encodes at least the variable domain of a complementary Ig light or heavy chain, respectively;

(c) transforming a cell line with the first or both prepared vectors; and (d) culturing said transformed cell line to produce said altered antibody.

The DNA sequence in step (a) may encode both the variable domain and/or each constant domain of the human antibody chain. The humanized antibody can be prepared using any suitable recombinant expression system. The cell line that is transformed to produce the altered antibody may be a Chinese Hamster Ovary (CHO) cell line or an immortalized mammalian cell line, which is advantageously of lymphoid origin, such as a myeloma, hybridoma, trioma or quadroma cell line. The cell line may also comprise a normal lymphoid cell, such as a B-cell, which has been immortalized by transformation with a virus, such as the Epstein-Barr virus. For example, the immortalized cell line is a myeloma cell line or a derivative thereof.

The CHO cells used for expression of the antibodies according to the invention may be dihydrofolate reductase (dhfr) deficient and so dependent on thymidine and hypoxanthine for growth. See Urlaub et al., 77 Proc. Natl. Acad. Sci. U.S.A. 4216-20 (1980). The parental dhfr CHO cell line is transfected with the DNA encoding the antibody and dhfr which enables selection of CHO cell transfectants of dhfr positive phenotype. Selection is carried out by culturing the colonies on media devoid of thymidine and hypoxanthine, the absence of which prevents untransfected cells from growing and transformed cells from resalvaging the folate pathway and thus bypassing the selection system. These transfectants usually express low levels of the DNA of interest by virtue of co-integration of transfected DNA of interest and DNA encoding dhfr. The expression levels of the DNA encoding the antibody may be increased by amplification using methotrexate (MTX). This drug is a direct inhibitor of the enzyme dhfr and allows isolation of resistant colonies which amplify their dhfr gene copy number sufficiently to survive under these conditions. Since the DNA sequences encoding dhfr and the antibody are closely linked in the original transfectants, there is usually concomitant amplification, and therefore increased expression of the desired antibody.

Another expression system for use with CHO or myeloma cells is the glutamine synthetase (GS) amplification system described in U.S. Pat. No. 5,122,464. This system involves the transfection of a cell with DNA encoding the enzyme GS and with DNA encoding the desired antibody. Cells are then selected which grow in glutamine free medium and can thus be assumed to have integrated the DNA encoding GS. These selected clones are then subjected to inhibition of the enzyme GS using methionine sulphoximine (Msx). The cells, in order to survive, will amplify the DNA encoding GS with concomitant amplification of the DNA encoding the antibody.

Although the cell line used to produce the humanized antibody may be a mammalian cell line, any other suitable cell line, such as a bacterial cell line or a yeast cell line, may alternatively be used. For example, in instances requiring no in vivo post-translational modification (such as instances where glycosylation is not required), it is envisaged that $E.$ $coli$-derived bacterial strains could be used. The antibody obtained is checked for functionality. If functionality is lost, it is necessary to return to step (2) and alter the framework of the antibody.

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIFICATION (Springer-Verlag, NY, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized antibody may then be used therapeutically or in developing and performing assay procedures, immunofluorescent stainings, and the like. See generally, Vols. I & II Immunological Methods, (Lefkovits & Pernis, eds., Academic Press, NY, 1979 and 1981).

Phage Libraries and Alternative Recombinant Expression Systems

Along with the above production techniques, in vitro systems such as phage display methods of fully human antibodies and antibody peptides, many of the benefits of human antibodies as both diagnostics and therapeutics are now being realized.

The recombinant antibody and its sequences of the present invention allows for the construction of a myriad of derivatives and ligand binding molecules with anti-PCAA binding activity. For example, the CDRs may be recombined with an antibody library such as the n-CoDeR human scFV library to create highly specific and functional antibody fragments. See Moore, 426 Nature, 725-31 (2003).

A library of fully human antibodies or portions thereof may also be created following the cloning methods based on site specific cleavage of single-stranded DNAs as described by U.S. Patent Appl. Ser. No. 20030232333.

Another ligand binding molecule that may be constructed from the DNA sequence information contained herein, and the associated knowledge gained about the PCAA epitopes provided by the invention herein, involves the construction of ANTICALINS® (lipocalins, muteins). ANTICALINS are derived from lipocalins, a widespread group of small and robust proteins that are usually involved in the physiological transport or storage of chemically sensitive or insoluble compounds. Several natural lipocalins occur in human tissues or body liquids. Despite low mutual sequence homology, the lipocalins share a structurally conserved β-barrel supporting four loops at one end, which form the entrance to a binding pocket. The loops exhibit large conformational differences between individual lipocalins and give rise to the variety of natural ligand specificities. This protein architecture is reminiscent of immunoglobulins, with their hypervariable loops on top of a rigid framework. Unlike antibodies or some antibody fragments, lipocalins are composed of a single polypeptide chain with 160 to 180 amino acid residues, being just marginally bigger than a single immunoglobulin domain. The set of four loops that makes up the binding pocket shows structural plasticity and tolerates a variety of side chains. The binding site can thus be reshaped in order to recognize prescribed target molecules of different shape with high affinity and specificity. ANTICALINS® have been engineered that recognize hapten-like compounds, peptides, and protein targets, e.g. extracellular domains of cell surface receptors. Fusion proteins with enzymes and also bispecific binding proteins (so-called DUOCALINS®) have also been successfully prepared. Preclinical experiments have been conducted. See, e.g., Korndörfer et al., 330 J. Mol. Biol. 385-96 (2003).

Another antibody type with application to the invention described herein include the camilid immunoglobulins which possess functional heavy chains and lack light chains. These antibodies are assembled from dedicated V and C gamma genes. They have been cloned and adapted using phage display technology to produce antigen-specific single-domain antibody fragments with intrinsic high stability. U.S. Patent Appl. Pub. No. 2003/0088074.

Another relevant derivative takes advantage of new technology for providing bacterially produced antibody fragments that can crosslink antigen and antibody effector molecules (Fc-region molecules), called Pepbodies™. U.S. Patent Appl. Pub. No. 20040101905. Hence, the binding molecules comprising the antigen binding site of the anti-PCAA site is genetically fused to peptides that display one or more of the effector functions associated with the Fc-region, and provides for functions such as interaction with cell receptors and complement activation.

The new antigen receptor (IgNAR) molecules from sharks may also be considered a "derivative" antibody molecule. The NAR is a disulphide bonded dimer of two protein chains, each containing one variable and five constant domains, and functions as an antibody. Nuttall et al., 270 Eur. J. Biochem., 3543-54 (2003). The sequences of the PCAA-binding antibody of the present invention may be constructed into the NAR variable region to create an in vitro library incorporating synthetic the CDR regions. This results in a single domain binding reagent.

One of the recent advances in cancer cell biology entails the discovery of progenitor cell lines that may exhibit cancer-cell markers. For example, human pancreatic epithelial progenitor cells have been identified and grown in culture. These cells may then be used for the generation of antigens useful, inter alfa, for the development of monoclonal antibodies. U.S. Pat. No. 6,436,704. Thus, the PCAA-binding antibody may be used to identify progenitor cells. These progenitor cells can be used as an immunogen that is administered to a heterologous recipient, such as a mouse, for derivation of further lines of PCAA-binding antibodies.

In conclusion, the oligonucleotide and amino acid sequences provided herein enable a myriad of possible molecules with CPAA-binding activity, and the scope of the present invention is not limited by the methods of achieving those molecules.

Antibody Derivatives

A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labelled monoclonal antibodies that are labeled, for example, with radioactive iodine ($^{125}$I, $^{131}$I), carbon ($^{14}$C), sulfur ($^{35}$S), tritium ($^{3}$H) or the like; conjugates of monoclonal antibodies with biotin or avidin, with enzymes, such as horseradish peroxidase, alkaline phosphatase, β-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins). An example of a derivative of the antibody of the invention is an antibody-small molecule drug conjugate, such as an antibody-maytansinoid conjugate, that displays cytotoxic activity. See U.S. Patent Appl. Pub. No. 20040039176. Preclinical evaluation has shown that this conjugate acts as a tumor-activated prodrug that exhibits potent antitumor activity in xenograft models. Further cytotoxic antibody derivatives are discussed below.

Another derivative bifunctional antibody of the present invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (e.g., by lengthening the time to clearance from the blood stream. Such techniques include, for example, adding PEG moieties (also termed pegilation), and are well-known in the art. See U.S. Patent. Appl. Pub. 20030031671.

Anti-Idiotype Abs

In addition to monoclonal or chimeric anti-CPAA antibodies, the present invention is also directed to an anti-idiotypic (anti-Id) antibody specific for the anti-CPAA antibody of the invention. An anti-Id antibody is an antibody which recognizes unique determinants generally associated with the antigen-binding region of another antibody. The antibody specific for CPAA is termed the idiotypic or Id antibody. The anti-Id can be prepared by immunizing an animal of the same species and genetic type (e.g. mouse strain) as the source of the Id antibody with the Id antibody or the antigen-binding region thereof. The immunized animal will recognize and respond to the idiotypic determinants of the immunizing antibody and produce an anti-Id antibody. The anti-Id antibody can also be used as an "immunogen" to induce an immune response in yet another animal, producing a so-called anti-anti-Id antibody. The anti-anti-Id can be epitopically identical to the original antibody which induced the anti-Id. Thus, by using antibodies to the idiotypic determinants of a mAb, it is possible to identify other clones expressing antibodies of identical specificity.

Accordingly, monoclonal antibodies generated against CPAA according to the present invention can be used to induce anti-Id antibodies in suitable animals, such as BALB/c mice. Spleen cells from such immunized mice can be used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a CPAA epitope.

Idiotypes, Anti-Idiotypes

Additionally, antibodies against CPAA, its analogs, portions, fragments, peptides or derivatives thereof may be used to induce anti-Id antibodies in suitable animals, such as BALB/c mice. Spleen cells from such immunized mice are used to produce anti-Id hybridomas secreting anti-Id monoclonal antibodies. Further, the anti-Id antibodies can be coupled to a carrier such as keyhole limpet hemocyanin (KLH) and used to immunize additional BALB/c mice. Sera from these mice will contain anti-anti-Id antibodies that have the binding properties of the original monoclonal antibody specific for an epitope of CPAA, or analogs, fragments and derivatives thereof. The anti-Id antibodies thus have their own idiotypic epitopes, or "idiotopes" structurally similar to the epitope being evaluated.

An anti-idiotypic (anti-Id) antibody is an antibody that recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, e.g., U.S. Pat. No. 4,699,880 and U.S. Pat. No. 6,835,823. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Structural Analogs of Anti-CPAA Antibodies and Anti-CPAA Peptides

Structural analogs of anti-CPAA antibodies and peptides of the present invention are provided by known method steps based on the teaching and guidance presented herein.

Knowledge of the three-dimensional structures of proteins is crucial in understanding how they function. The three-dimensional structures of hundreds of proteins are currently available in protein structure databases (in contrast to the thousands of known protein sequences in sequence databases). Analysis of these structures shows that they fall into recognizable classes of motifs. It is thus possible to model a three-dimensional structure of a protein based on the protein's homology to a related protein of known structure. Many examples are known where two proteins that have relatively low sequence homology, can have very similar three dimensional structures or motifs.

In recent years it has become possible to determine the three dimensional structures of proteins of up to about 15 kDa by nuclear magnetic resonance (NMR). The technique only requires a concentrated solution of pure protein. No crystals or isomorphous derivatives are needed. The structures of a number of proteins have been determined by this method. The details of NMR structure determination are well-known in the art. See, e.g., Wuthrich, NMR of Proteins & Nucleic Acids (Wiley, N.Y., 1986); Wuthrich, 243 Science 45-50 (1989); Clore et al., 24 Crit. Rev. Bioch. Molec. Biol. 479-564 (1989); Cooke et al., 8 Bioassays 52-56 (1988).

In applying this approach, a variety of $^1$H NMR 2D data sets are collected for anti-CPAA antibodies and/or anti-CPAA peptides of the present invention. These are of two main types. One type, COSY (Correlated Spectroscopy) identifies proton resonances that are linked by chemical bonds. These spectra provide information on protons that are linked by three or less covalent bonds. NOESY (nuclear Overhauser enhancement spectroscopy) identifies protons which are close in space (less than 0.5 nm). Following assignment of the complete spin system, the secondary structure is defined by NOESY. Cross peaks (nuclear Overhauser effects or NOE's) are found between residues that are adjacent in the primary sequence of the peptide and can be seen for protons less than 0.5 nm apart. The data gathered from sequential NOE's combined with amide proton coupling constants and NOE's from non-adjacent amino acids that are adjacent to the secondary structure, are used to characterize the secondary structure of the peptides. Aside from predicting secondary structure, NOE's indicate the distance that protons are in space in both the primary amino acid sequence and the secondary structures. Tertiary structure predictions are determined, after all the data are considered, by a "best fit" extrapolation.

Types of amino acids are first identified using through-bond connectivities. Next, specific amino acids are assigned using through-space connectivities to neighboring residues, together with the known amino acid sequence. Structural information is then tabulated and is of three main kinds: The NOE identifies pairs of protons which are close in space, coupling constants give information on dihedral angles and slowly exchanging amide protons give information on the position of hydrogen bonds. The restraints are used to compute the structure using a distance geometry type of calculation followed by refinement using restrained molecular dynamics. The output of these computer programs is a family of structures which are compatible with the experimental data (i.e. the set of pairwise<0.5 nm distance restraints). The better that the structure is defined by the data, the better the family of structures can be superimposed, (i.e., the better the resolution of the structure). In the better defined structures using NMR, the position of much of the backbone (i.e. the amide, Ca and carbonyl atoms) and the side chains of those amino acids that lie buried in the core of the molecule can be defined as clearly as in structures obtained by crystallography. The side chains of amino acid residues exposed on the surface are frequently less well defined, however. This probably reflects the fact that these surface residues are more mobile and can have no fixed position. (In a crystal structure this might be seen as diffuse electron density).

Thus, according to the present invention, use of NMR spectroscopic data is combined with computer modeling to arrive at structural analogs of at least portions of anti-CPAA antibodies and peptides based on a structural understanding of the topography. Using this information, one of ordinary skill in the art will know how to achieve structural analogs of anti-CPAA antibodies or peptides, such as by rationally-based amino acid substitutions allowing the production of peptides in which the CPAA binding affinity or avidity is modulated in accordance with the requirements of the expected therapeutic or diagnostic use of the molecule, for example, the achievement of greater specificity for CPAA binding.

Alternatively, compounds having the structural and chemical features suitable as anti-CPAA therapeutics and diagnostics provide structural analogs with selective CPAA affinity. Molecular modeling studies of CPAA binding compounds, such as CPAA receptors, anti-CPAA antibodies, or other CPAA binding molecules, using a program such as MACROMODEL®, INSIGHT®, and DISCOVER® provide such spatial requirements and orientation of the anti-CPAA Abs and/or peptides according to the present invention. Such structural analogs of the present invention thus provide selective qualitative and quantitative anti-CPAA activity in vitro, in situ and/or in vivo.

Diagnostic Applications

The present invention also provides the above anti-CPAA antibodies and peptides for use in diagnostic methods for detecting CPAA in patients known to be or suspected of having pancreatic or colon carcinoma. In another aspect of the invention, the antibodies may detect molecular markers in morphologically normal cells to provide for early detection screening of disease-free individuals.

Anti-CPAA antibodies and/or peptides of the present invention are useful for immunoassays which detect or quantitate CPAA, or anti-CPAA antibodies, in a sample. An immunoassay for CPAA typically comprises incubating a clinical or biological sample in the presence of a detectably labeled high affinity (or high avidity) anti-CPAA antibody or polypeptide of the present invention capable of selectively binding to CPAA, and detecting the labeled peptide or antibody which is bound in a sample. Various clinical assay procedures are well known in the art. See, e.g., Immunoassays for the 80's (Voller et al., eds., University Park, 1981). Such samples include tissue biopsy, blood, serum, and fecal samples, or liquids collected from the colorectal track following enema or oral laxative solution and subjected to ELISA analysis as described below.

Thus, an anti-CPAA antibody or polypeptide can be fixed to nitrocellulose, or another solid support which is capable of immobilizing cells, cell particles or soluble proteins. The support can then be washed with suitable buffers followed by treatment with the detectably labeled CPAA-specific peptide or antibody. The solid phase support can then be washed with the buffer a second time to remove unbound peptide or antibody. The amount of bound label on the solid support can then be detected by known method steps.

"Solid phase support" or "carrier" refers to any support capable of binding peptide, antigen, or antibody. Well-known supports or carriers, include glass, polystyrene, polypropylene, polyethylene, polyvinyl fluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to CPAA or an anti-CPAA antibody. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, peptide or antigen, or can ascertain the same by routine experimentation.

Well known method steps can determine binding activity of a given lot of anti-CPAA peptide and/or antibody. Those skilled in the art can determine operative and optimal assay conditions by routine experimentation.

Detectably labeling a CPAA-specific peptide and/or antibody can be accomplished by linking to an enzyme for use in an enzyme immunoassay (EIA), or enzyme-linked immunosorbent assay (ELISA). The linked enzyme reacts with the exposed substrate to generate a chemical moiety which can be detected, for example, by spectrophotometric, fluorometric or by visual means. Enzymes which can be used to detectably label the CPAA-specific antibodies of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the CPAA-specific antibodies, it is possible to detect CPAA through the use of a radioimmunoassay (RIA). See Work et al., LABORATORY TECHNIQUES & BIOCHEMISTRY IN MOLECULAR BIOLOGY (North Holland Publishing Co., N.Y. (1978). The radioactive isotope can be detected by such means as the use of a gamma counter or a scintillation counter or by autoradiography. Isotopes which are particularly useful for the purpose of the present invention are: $^{3}H$, $^{125}I$, $^{131}I$, $^{35}S$, $^{14}C$, and $^{125}I$.

It is also possible to label the CPAA-specific antibodies with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The CPAA-specific antibodies can also be detectably labeled using fluorescence-emitting metals such as $^{125}Eu$, or others of the lanthanide series. These metals can be attached to the CPAA-specific antibody using such metal chelating groups as diethylenetriaminepentaacetic acid (DTPA) or ethylenediamine-tetraacetic acid (EDTA).

The CPAA-specific antibodies also can be detectably labeled by coupling to a chemiluminescent compound. The presence of the chemiluminescently labeled antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the CPAA-specific antibody, portion, fragment, polypeptide, or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the CPAA-specific antibody, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the CPAA which is detected by the above assays can be present in a biological sample. Any sample containing CPAA can be used. For example, the sample is a biological fluid such as, for example, blood, serum, lymph, urine, feces, inflammatory exudate, cerebrospinal fluid, amniotic fluid, a tissue extract or homogenate, and the like. However, the invention is not limited to assays using only these samples, it being possible for one of ordinary skill in the art to determine suitable conditions which allow the use of other samples.

In situ detection can be accomplished by removing a histological specimen from a patient, and providing the combination of labeled antibodies of the present invention to such a specimen. The antibody (or fragment) may be provided by applying or by overlaying the labeled antibody (or fragment) to a biological sample. Through the use of such a procedure, it is possible to determine not only the presence of CPAA but also the distribution of CPAA in the examined tissue. Using the present invention, those of ordinary skill will readily perceive that any of a wide variety of histological methods (such as staining procedures) can be modified in order to achieve such in situ detection.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical, immunometric assays include "forward" assays in which the antibody bound to the solid phase is first contacted with the sample being tested to extract the CPAA from the sample by formation of a binary solid phase antibody-CPAA complex. After a suitable incubation period, the solid support is washed to remove the residue of the fluid sample, including unreacted CPAA, if any, and then contacted with the solution containing a known quantity of labeled antibody (which functions as a "reporter molecule"). After a second incubation period to permit the labeled antibody to complex with the CPAA bound to the solid support through the unlabeled antibody, the solid support is washed a second time to remove the unreacted labeled antibody. This type of forward sandwich assay can be a simple "yes/no" assay to determine whether CPAA is present or can be made quantitative by comparing the measure of labeled antibody with that obtained for a standard sample containing known quantities of CPAA. Such "two-site" or "sandwich" assays are described by Wide, Radioimmune Assay Methods, 199-206 (Kirkham, ed., Livingstone, Edinburgh, 1970).

Other type of "sandwich" assays, which can also be useful with CPAA, are the so-called "simultaneous" and "reverse" assays. A simultaneous assay involves a single incubation step wherein the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes can be used to construct a sensitive three-site immunoradiometric assay.

Additionally, the exemplary antibodies can be utilized for T-cell typing, for isolating specific CPAA-bearing cells or fragments, for vaccine preparation, or the like. The antibodies may be used to quantitatively or qualitatively detect the CPAA in a sample or to detect presence of cells that express the CPAA. This can be accomplished by immunofluorescence techniques employing a fluorescently labeled antibody (see below) coupled with fluorescence microscopy, flow cytometric, or fluorometric detection. For diagnostic purposes, the antibodies may either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays, such as those discussed previously are available and are well known to those skilled in the art.

The antibodies useful in the present invention may be employed histologically, as in immunofluorescence or immunoelectron microscopy, for in situ detection of the CPAA of the present invention. In situ detection may be accomplished by removing a histological specimen from a patient, and providing the labeled antibody of the present invention to such a specimen. The antibody (or fragment) may be provided by applying or by overlaying the labeled antibody (or fragment) to a biological sample. Through the use of such a procedure, it is possible to determine not only the presence of the CPAA but also its distribution on the examined tissue. Using the present invention, those of ordinary skill will readily perceive that any of wide variety of histological methods (such as staining procedures) can be modified in order to achieve such in situ detection.

Importantly, the antibodies of the present invention may be helpful in diagnosing the invasiveness of certain types of colorectal and pancreatic cancer. More specifically, the antibody of the present invention may identify CPAA present in patients with slow cancers that grow over several years as opposed to aggressive cancers that progress much faster. Thus, the antibody of the present invention may provide an important immunohistochemistry tool.

The antibodies of the present invention may be used on antibody arrays, highly suitable for measuring gene expression profiles including post-translational modification and also useful for detecting smaller molecules such as peptide hormones and carbohydrates. Several approaches have recently been employed to determine the suitability and efficacy of antibody arrays. In some instances, phage-displayed antibodies have been used in preparing the arrays, and detection and analysis is done by SELDI (surface-enhanced laser desorption/ionization), or in a high-throughput format by filter-based enzyme-linked immunosorbent assay (ELISA). Other examples of detection systems include fluorescent tags and nanoelectrodes, and for smaller arrays, surface plasmon resonance and MALDI-TOF (matrix-assisted laser desorption ionization-time of flight) mass spectrometry. Proteome analysis can also be performed by first generating an array of bound antigens followed by antibody capture and detection with an affinity ligand such as Protein L or Protein A bound to a detection probe.

A third approach involves high-density gridding of bacteria containing antibody genes onto a filter followed by interaction with another filter containing an affinity ligand or the antigen attached with a detection probe such as ELISA. This method eliminates the need for liquid handling, and parallel screens of tens of thousands of antibodies against multiple antigens can be performed to identify ultimately proteins that are differentially expressed. A final method involves the possibility of synthesizing antibodies directly on the chip using combinatorial chemistry. Current technology, however, somewhat strained at synthesizing even the antigen-binding antibody domains that consists of a minimum of 120 aminoacids, unless presynthesized polypeptide building blocks are used to create an antibody framework followed by the addition of individual amino acids.

Screening methods for determining anti-CPAA activities are also provided for in the present invention. Specifically, as described further in Example 6, the antibody of the present invention is associated with antibody-dependent cellular cytotoxicity (ADCC) activity. Anti-CPAA compounds that can be selected from the group consisting of antibodies, or fragments or portions thereof, peptides, peptido mimetic compounds or organo mimetic compounds that trigger death of CPAA-bearing cells in vitro, in situ or in vivo are encompassed by the present invention. Screening methods which can be used to determine ADCC activity of an anti-CPAA compound can include in vitro or in vivo assays. Such in vitro assays can include a CPAA cytotoxicity assay, such as a radioimmuno assay, which determines a decrease in cell death by contact with CPAA, such as chimpanzee or human CPAA in isolated or recombinant form, wherein the concurrent presence of a CPAA neutralizing compound reduces the degree or rate of cell death.

Diagnostic Kits

Kits can also be supplied for use with the subject antibodies in the protection against or detection of a cellular activity or for the presence of a selected antigen. Thus, an antibody of the present invention may be provided, usually in a lyophilized form in a container, either alone or in conjunction with additional antibodies specific for the desired cell type. The antibodies, which may be conjugated to a label or toxin, or unconjugated, are included in the kits with buffers, such as Tris, phosphate, carbonate, etc., stabilizers, biocides, inert proteins, e.g., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1% to 99% wt. of the total composition. Where a second antibody capable of binding to the primary antibody is employed in an assay, this will usually be present in a separate vial. The second antibody is typically conjugated to a label and formulated in an analogous manner with the antibody formulations described above. The kit will generally also include a set of instructions for use.

Pharmaceutical Applications

The anti-CPAA antibodies or peptides of the present invention can be used for example in the treatment of carcinomas and related conditions. More specifically, the invention further provides for a pharmaceutical composition comprising a pharmaceutically acceptable carrier or diluent and, as active ingredient, an antibody or peptide according to the invention. The delivery component of the immunotoxin is a humanized antibody according to the present invention. Intact immunoglobulins or their binding fragments, such as Fab, are also envisioned. Typically, the antibodies in the immunotoxins will be of the human IgA, IgM or IgG isotype, but other mammalian constant regions may be utilized as desired. The composition may also comprise an immunotoxin according to the invention. The humanized antibody, immunotoxin and pharmaceutical compositions thereof of this invention are useful for parenteral administration, i.e., subcutaneously, intramuscularly or intravenously.

Anti-CPAA antibodies and/or peptides of the present invention can be administered either as individual therapeutic agents or in combination with other therapeutic agents. They can be administered alone, but are generally administered with a pharmaceutical carrier selected on the basis of the chosen route of administration and standard pharmaceutical practice.

For parenteral administration, anti-CPAA antibodies or peptides can be formulated as a solution, suspension, emulsion or lyophilized powder in association with a pharmaceutically acceptable parenteral vehicle. For example the vehicle may be a solution of the antibody or a cocktail thereof dissolved in an acceptable carrier, such as an aqueous carrier such vehicles are water, saline, Ringer's solution, dextrose solution, or 5% human serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (e.g., sodium chloride, mannitol) and chemical stability (e.g., buffers and preservatives). The formulation is sterilized by commonly used techniques.

Thus, a typical pharmaceutical composition for intramuscular injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, Remington's Pharmaceutical Science (15th ed., Mack Pub. Co., Easton, Pa., 1980).

The antibodies of this invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present human-like antibodies or a cocktail thereof can be administered for prevention of recurrence and/or therapeutic treatments for existing disease. Suitable pharmaceutical carriers are described in the most recent edition of Remington's Pharmaceutical Sciences, a standard reference text in this field of art. For example, a parenteral composition suitable for administration by injection is prepared by dissolving 1.5% by weight of active ingredient in 0.9% sodium chloride solution. Anti-CPAA peptides and/or antibodies of this invention can be adapted for therapeutic efficacy by virtue of their ability to mediate antibody-dependent cellular cytotoxicity (ADCC), and/or apoptosis, and/or complement-dependent cytotoxicity (CDC) against cells having CPAA associated with their surface. For these activities, either an endogenous source or an exogenous source of effector cells (for ADCC) or complement components (for CDC) can be utilized.

In therapeutic application, compositions are administered to a patient already suffering from a disease, in an amount sufficient to cure or at least partially arrest or alleviate the disease and its complications. An amount adequate to accomplish this is defined as a "therapeutically effective dose." Amounts effective for this use will depend upon the severity of the malignancy and the general state of the patient's own immune system, but generally range from about 1 mg to about 200 mg of antibody per dose, with dosages of from 5 mg to 25 mg per patient being more commonly used. It must be kept in mind that the materials of the invention may generally be employed in serious disease states, often life-threatening or potentially life-threatening situations. In such cases, in view of the minimization of extraneous substances and the lower probability of "foreign substance" rejections which are achieved by the present human-like antibodies of this invention, it is possible and may be felt desirable by the treating physician to administer substantial excesses of these antibodies.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily, weekly, or biweekly dosage of active ingredient can be about 100 mg/m$^2$ to 250 mg/m$^2$ of body weight delivered over a 4 hour to 6 hour period.

As a non-limiting example, treatment of CPAA-related pathologies humans or animals can be provided as a daily, weekly, or biweekly dosage of anti-CPAA peptides, monoclonal chimeric and/or murine antibodies of the present invention in a dosage range from 0.1 mg/kg to 100 mg/kg, per day, weekly, or biweekly.

Example antibodies for human therapeutic use are high affinity (these may also be high avidity) murine and chimeric antibodies, and fragments, regions and derivatives having potent in vivo anti-CPAA activity, according to the present invention.

Dosage forms (composition) suitable for internal administration generally contain from about 0.1 milligram to about 500 milligrams of active ingredient per unit. In these pharmaceutical compositions the active ingredient will ordinarily be present in an amount of about 0.5-95% by weight based on the total weight of the composition.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

The antibodies can also be used as separately administered compositions given in conjunction with chemotherapeutic or immunosuppressive agents. Typically, the agents will include cyclosporin A or a purine analog (e.g., methotrexate, 6-mercaptopurine, or the like), but numerous additional agents (e.g., cyclophosphamide, prednisone, etc.) well-known to those skilled in the art may also be utilized.

An antibody of the present invention may form part of an immunotoxin. Immunotoxins are characterized by two components and are useful for killing selected cells in vitro or in vivo. One component is a cytotoxic agent which is usually fatal to a cell when attached or absorbed. The second component, known as the "delivery vehicle", provides a means for delivering the toxic agent to a particular cell type, such as cells comprising a carcinoma. The two components are commonly chemically bonded together by any of a variety of well-known chemical procedures. For example, when the cytotoxic agent is a protein and the second component is an intact immunoglobulin, the linkage may be by way of heterobifunctional cross-linkers, e.g., SPDP, carbodiimide, glutaraldehyde, or the like. Production of various immunotoxins is well-known with the art, and can be found, for example in Thorpe et al., "Monoclonal Antibody-Toxin Conjugates: Aiming the Magic Bullet," Monoclonal Antibodies in Clinical Medicine, 168-190 (Academic Press, 1982).

A variety of cytotoxic agents are suitable for use in immunotoxins. Cytotoxic drugs interfere with critical cellular processes including DNA, RNA, and protein synthesis. Cytotoxic agents can include radionuclides, such as include $^{212}$Bi, $^{131}$I, $^{188}$Re, and $^{90}$Y; a number of chemotherapeutic drugs, such as vindesine, methotrexate, adriamycin, and cisplatin; and cytotoxic proteins such as ribosomal inhibiting proteins like pokeweed antiviral protein, *Pseudomonas* exotoxin A, ricin, diphtheria toxin, ricin A chain, etc., or an agent active at the cell surface, such as the phospholipase enzymes (e.g., phospholipase C). See, generally, Olsnes & Phil "Chimeric Toxins," 25 Pharmac. Ther., 335-81 (1982); "Monoclonal Antibodies for Cancer Detection and Therapy," 159-79, 224-66 (Baldwin & Byers eds., Academic Press, 1985).

The antibodies or peptides and derivatives can be used therapeutically as immunoconjugates. See Dillman, 111 Ann. Int. Med. 592-603 (1989). Such antibodies or polyeptides can be coupled to cytotoxic proteins, including, but not limited to ricin-A, *Pseudomonas* toxin and *Diphtheria* toxin. Toxins conjugated to antibodies or other ligands or peptides are well known in the art. See, e.g., Olsnes et al., 10 Immunol. Today 291-95 (1989). Plant and bacterial toxins typically kill cells by disrupting the protein synthetic machinery. Cytotoxic drugs that can be conjugated to anti-CPAA peptides and/or antibodies and subsequently used for in vivo therapy include, but are not limited to, daunorubicin, doxorubicin, methotrexate, and Mitomycin C. For a description of these classes of drugs which are well known in the art, and their mechanisms of action, see Goodman & Gilman's THE PHARMACOLOGICAL BASIS OF THERAPEUTICS (8th Ed., Macmillan Publishing Co., 1990).

Additionally, the antibody of the present invention may be delivered in combination with chemotherapeutic agents such as oxaliplatin, irinotecan, topotecan, leucovorin, carmustine, vincristine, fluorouracil, streptozocin, and gemcitabine. Combinations of other antibodies and such compounds have been used in advanced colorectal cancer patients. See, e.g., U.S. Patent Appl. Pub. No. 2002/0187144.

Anti-CPAA antibodies and/or peptides of this invention can be advantageously utilized in combination with other monoclonal or murine and chimeric antibodies, fragments and regions, or with lymphokines or hemopoietic growth factors, etc., which serve to increase the number or activity of effector cells which interact with the antibodies. For example, the antibody of the present invention may be co-administered with human monoclonal antibodies reactive with other markers on cells responsible for the disease. For example, suitable T-cell markers can include those grouped into the so-called "Clusters of Differentiation" as named by the First International Leukocyte Differentiation Workshop, Leukocyte Typing (Bernard et al., eds., Springer-Verlag, N.Y., 1984).

Cancer Vaccine

Another aspect of the present invention provides for a cancer vaccine. By "vaccine" is meant an agent used to stimulate the immune system of a living organism. In this regard, the immune response may provide for prophylaxis or may provide for a positive effect in a diseased organism by, for example, alleviating an existing condition. Specifically, a cancer vaccine is meant to therapeutically treat existing malignancy and/or to prevent the progression or metastasis of an existing malignancy.

That specific active immunotherapy can be achieved using tumor-associated antigens is widely known. Indeed, the initial, roughly-purified antigenic preparations used to derive the monoclonal antibody that has allowed the further invention presented herein was shown to provide for protective immunity in humans. Hollinshead et al., 1985. At that time, patients had undergone tumor resection and were then vaccinated with antigenic material derived from tumor membranes in the amount of 200 µg, 300 µg, or 500 µg in 0.2 ml dispersions mixed with an additional 0.2 ml Freund's adjuvant. Dosages of 300 µg given monthly for three months were shown to be safe.

With the recombinant antibodies described herein, it is now possible to define a highly purified antigen or epitope peptides of CPAA that is further suitable for a vaccine against these cancers. For example, NPC-1 may be used to bind to tissue or cell samples from which the CPAA protein and its corresponding amino acid sequence may be identified by any number of known techniques. The epitope may be mapped further, and the molecular nature determined with exquisite detail. See, e.g, Baerga-Oritz et sl., "Epitope mapping of a monoclonal antibody against human thrombin by H/D-exchange mass spectropmetry reveals selection of a divers sequence in a highly conserved sequence," 11 Protein Sci. 1300-08 (2002); Jemmerson, & Paterson, "Mapping antigenic sites on proteins: implications for the design of synthetic vaccines," 4 BioTechniques 18-31 (1986).

An alternative technique to identify effective antigenic peptides entails using the NPC-1 antibody or peptide to screen an expression library (such as a phage display library) for mimetic proteins, or mimotopes, that are recognized by the antibody. This technique has been used to identify antigenic peptides that have raised protective immune responses in vivo. See Beenhouwer et al., 169 J. Immunol. 6992-99 (2002); see also U.S. Pat. No. 5,837,550; Visvanathan et al., 48 Arthritis & Rheumatism, 737-45 (2003); Sato et al., 371 Biochem. J. 603-08 (2003). Note that this technique has been used to identify protein mimetics of carbohydrate and glycoprotein antigens, the protein versions found to be more immunogenic than the natural carbohydrate counterparts. Indeed, mimetics may be isolated that are advantageous over known antigens because of factors including production capacity, safety, half-life, or other issues.

The CPAA immunogenic protein may be prepared and delivered, for example, as either a subcutaneous or a mucosal vaccine alone, or associated with an adjuvant or carrier or as part of an adjuvant or protein conjugate. Delivery by liposomes microparticles, virus-like particles, DNA vaccines, live recombinant vectors such as *Salmonella typhimurium*, and possibly ISCOMs are envisioned. All of these systems are well-known by those of ordinary skill in the art, and may be practiced without undue experimentation. See, e.g., Michalek et al., "Antigen Delivery Systems I: Nonliving Microparticles, Liposome, and Immune Stimulating Complexes (ISCOMs)," in MUCOSAL IMMUNOLOGY (Mestecky et al., eds., Elsevier, 2005).

Additionally, the CPAA peptide may be genetically or chemically conjugated to a toxoid carrier, such as cholera, entero, or ricin toxoid. See, e.g., U.S. Pat. No. 6,846,488. Another advantageous protein carrier derived from bacterium is the PorB protein carrier. See e.g., U.S. Pat. No. 6,613,336. Another promising protein-based mucosal adjuvant is the flagellin protein from *S. typhimurium*. In an embodiment of the invention, the CPAA protein is co-administered with the flagellin protein (FljB) via, for example, the mucosal intranasal route. An advantageous protein platform comprising duck hepatitis core antigen is also presented in U.S. Patent Appl. Pub. No. 2004/0219164.

The CPAA of the present invention may also be delivered as a DNA vaccine for in vivo expression of the immunogenic construct. For example, cationic microparticles may be used to deliver the DNA expression cassette in intranasal vaccination. Such systems have induced an immune response following, for example, intranasal delivery of vaccine comprising DNA encoding the HIV-1 gag protein. Michalek et al., 2005. In an embodiment of the present invention, the CPAA immunogenic peptide is delivered via a DNA expression cassette which is subsequently expressed in vivo.

Additionally, the immunogenic preparation may be used to "charge" donor derived dendritic cells ex vivo, which are then returned to the patient where they home to the lymphoid organs and mount an effective immune response. See, e.g., Baar, J. "Clinical applications of dendritic cell cancer vaccines," 4(2) Oncologist, 140-44 (1999). This vaccine approach is currently in human trials for treating, for example, melanoma. More information can be found at the Dartmouth-Hitchcock Medical Center website, under Clinical Trials. Alternatively, a DNA vaccine as described above may be delivered via skin patch to the cells of Langerhans, which then mature to dendritic cells and home to the lypmphoid organs. U.S. Pat. No. 6,420,176.

Delivery of the immunogenic compositions of the present invention may be by parenteral, subcutaneous, or intramuscular injection, intravenous injection, intestinal, intradermal, intubation, or nasal, oral or rectal vaccination. The vaccine may also be delivered topically, including intranasal, upon the palatine tonsil, or delivery to the salivary glands. Administration of a vaccine contemplated by the present invention to the patient may be by any known or standard techniques.

The invention will now be described further by non-limiting examples.

EXAMPLES

Example 1

Preparation of Pancreatic and Colorectal Carcinoma-Associated Antigen (CPAA) from Human Tumor Specimens An immunogenic tumor associated antigen preparation was obtained from pooled colorectal carcinoma membranes according to the method described by Hollinshead et al., 56 Cancer 480 (1985); U.S. Pat. No. 5,688,657. This antigenic material was purified to the extent that the membrane fractions were free of HL-A antigens and were separated from much of the non-immunogenic glycoprotein fractions.

Tumor cell suspensions in saline were prepared from fresh operating room specimens. Single cell suspensions, obtained by mincing solid tumors, were centrifuged for 10 minutes at 400× gravity and the supernatant was retained. The cell pellet was resuspended in phosphate buffered saline (PBS) and re-centrifuged. The membrane material was examined by electron microscopy to assure that only membrane material (and no intact cells) was present, and the protein content was measured by the Lowry method. The membrane material was next subjected to sequential low frequency sonication and resuspended as a soluble pool of membrane proteins. The soluble sonicates were separated by gel filtration on Sephadex-6200. Fractions of 2 milliliters (ml) were collected and the absorbance profile at 220 and 280 nanometers (nm) was recorded. Fractions comprising individual protein peaks were pooled, and the pools were concentrated by Diaflo ultrafiltration. Sephadex-G200 fractions IB and IIA, as defined by Hollinshead et al., 1985, were further purified by gradient polyacrylamide gel electrophoresis (PAGE). The fractions were tested for their ability to elicit positive delayed cutaneous hypersensitivity reactions in patients with colorectal carcinoma. Those fractions with immunogenic activity were said to contain colorectal carcinoma-associated antigens and were employed as immunogens and screening agents in the preparation of monoclonal antibodies.

By gradient PAGE, a double-banded antigen distinct from that of carcinoembryonic antigen (Gold et al., 122 J. Exp. Med. 467-81 (1965); Hollinshead et al., 1985) was identified and isolated. The bands comprising this antigen migrated 6.3 cm and 6.6 cm distant from tracking dye. Biochemical analysis of the antigen indicated that this protein was a glycoprotein. The molecular weight of the antigen was estimated based on the electrophoretic mobility of transferrin (6.4-6.5 cm) which has a molecular weight of 76.5 kDa.

Example 2

Immunization and Preparation of Hybridomas

Monoclonal antibodies against human colorectal and pancreatic carcinoma-associated antigens (CPAA) were obtained by the production and cloning of hybrids resulting from the fusion of mouse myeloma cells Sp2/0-Ag14 with spleen cells from BALB/c mice which had been immunized with the CPAA described above. Hybrid clones were established and reacted strongly with the CPAA and with two colon carcinoma cell lines (SW480 and SW620) when assayed by ELISA.

A. Immunization and Cell Fusion:

BALB/c mice were immunized by intraperitoneal injection of 50 µg of the CPAA described above emulsified in complete Freund's adjuvant, as described by Hollinshead in clinical trials (Hollinshead et al., 1985). Ten days later, the mice received an intravenous booster injection of the same amount of CPAA in saline. Mice were sacrificed three days later and a single cell splenocyte suspension was prepared. Cell fusion was performed by incubating 5e7 mouse spleen cells with 10e7 sP2/0-Ag14 myeloma cells in 40% polyethylene glycol (MW=1500).

B. Screening of Hybrid Clones:

An enzyme-linked immunosorbent assay (ELISA), described by Tsang et al., 77 JNCI 1175 (1986), was used for the detection of hybridoma clones producing antibodies specific for the CPAA. CPAA (100 ng/well) was immobilized on polystyrene microplates. Antibodies present in the test supernatants were allowed to bind to the immobilized antigens for one hour. The presence of the bound murine mAbs was detected with peroxidase-conjugated secondary antibodies, specific for mouse immunoglobulins. Wells were washed and then the chromogenic substrate for peroxidase, O-phenyldiamine was added. Wells showing color reactions yielding absorbances greater or equal to 0.500 units were scored as positive. Negative controls gave values of 0.01 to 0.09 absorbance units. Hybridoma wells scoring as positive by ELISA were selected for expansion and repeating the cell cloning procedure by the limiting dilution cloning method. Selection of positive mAb producing hybridoma cells was determined by ELISA. Positive monoclonal cells were expanded in culture and aliquots of the cells were frozen under liquid nitrogen for long term storage.

Example 3

Isotype of NPC-1 Monoclonal Antibody

Murine immunoglobulins are expressed from separate genes that encode the heavy chain (55 kD) and the light chain (25-29 kD). There are four heavy chains of the IgG subclass (IgG1, IgG2a, IgG2b, TgG3) and two light chains (Kappa, Lambda) that can rearrange to yield the repertoire of murine immunoglobulins.

The isotype of the NPC-1 mAb was determined using a commercial mouse isotyping kit (catalog no. RPN29, GE Healthcare (formerly Amersham Biosciences). The assay involves incubating the test hybridoma supernatant with the isotyping stick, which includes pre-blotted anti-mouse Ig specific antibodies in marked areas of the stick. Detection of the test material is by horseradish peroxidase-conjugated anti-mouse Ig antibody and development with the peroxidase substrate, OPD. A positive color reaction indicated the heavy chain and the light chain expressed by the hybridoma, thus describing the Ig isotype of the mAb. The NPC-1 mAb was determined to be an IgG1 heavy chain and a Kappa light chain.

Example 4

DNA Sequence and Uniqueness of the NPC-1 Antibody

The linear amino acid sequence of a mAb identified NPC-1 as unique in comparison to the all the sequences of which the Applicants were aware. The linear amino acid sequence was be determined by first determining the linear sequence of the DNA that encodes the polypeptide molecule. The DNA sequence encoding the NPC-1 mAb was determined and the open reading frame was translated into the amino acid sequence using the universal mammalian codon usage table, thus describing the linear sequence identity of the NPC-1 molecule.

Oligonucleotide primers used for the murine IgG1 heavy chain reverse transcription, PCR, and sequencing reactions derived from the Constant-1 region of the heavy chain described in GenBank (AB097849). Primers used for the murine kappa light chain reverse transcription, PCR, and sequencing reactions derived from the Constant region of the light chain described in GenBank (AB097848).

A. Isolation of the Nucleic Acid of NPC-1

RNA was isolated from the NPC-1 producing hybridoma cells using the commercially available RNeasy-Midi kit (catalog no. 74104, Qiagen) as instructed by the manufacturers. Four million hybridoma cells were centrifuged in a conical tube, and the cells were lysed to release the nuclear and cytosolic nucleic acids including the RNA. The RNA was then purified from the lysate using the RNeasy spin columns. The RNA was then eluted with water and analyzed for yield and purity by absorbance at 260 nm and 280 nm using a spectrophotometer. The RNA was stored at −80° C.

B. Preparation of the cDNA

The RNA (2 µg) was first reverse-transcribed to cDNA using a deoxynucleotide triphosphate dNTP mixture (dATP, dCTP, dGTP, dTTP), cDNA systhesis buffer, RNase inhibitor, reverse transcriptase enzyme, and oligonucleotide primers specific for the heavy (IgG1) and light (Kappa) chains of the NPC-1 isotype. The reagents were provided in a 5'/3' RACE Kit (catalog no. 03-353, Roche Applied Sciences). The reaction progressed for 60 minutes at 55° C., followed by 5 minutes at 85° C. The cDNA was then purified by spin column (catalog no. 1-732-668, Roche Applied Sciences) and subjected to polyadenylation using dATP and terminal transferase for 30 minutes at 37° C. The polyadenylation reagents were also provided in the 5'/3' RACE kit (Roche Applied Sciences). Finally, the target DNA (mouse IgG1 heavy chain and Kappa light chain) were amplified for sequencing by the polymerase chain reaction (PCR) as defined by the following reaction: polyA-tailed cDNA template, oligo dT anchor primer, dNTP mixture, reaction buffer, Expand High Fidelity Polymerase enzyme, and the specific oligonucleotides for either the IgG heavy chain or the Kappa light chain. Reagents for the PCR were obtained commercially (catalog no. 1-732-641, Roche Applied Sciences). The mixture was subjected to 94° C. for 2 minutes, followed by 10 cycles of: 15 seconds at 94° C., 30 seconds at 55° C., 40 seconds at 72° C., which was followed by twenty-five cycles of: 15 seconds at 94° C., 30 seconds at 55° C., 60 seconds at 72° C. Following this, the reactions were incubated for 7 minutes at 72° C. and then cooled to 4° C. The amplified heavy and light chain DNA fragments were then gel purified on a 1% agarose gel. The target DNA bands were excised from the gel and then purified from the agarose using QIAquick gel extraction kit (catalog no. 28704, Qiagen).

C. DNA Sequencing and Analysis

Amplified target DNA was subjected to sequencing reactions using the dideoxynucleotide incorporation method. The entire sequence of the IgG1 heavy chain and Kappa light chain were determined using the previous mentioned primers and reagents from Applied Biosystems (BigDye Terminator V1.1 Cycle Sequencing kit, Part 4346776). Automated sequencing analysis was performed using the ABI-377 and ABI-310 DNA sequencers. The DNA sequence was translated in three reading frames and the frame without stop codons and that aligned homologously with other murine heavy and light chains was determined to be the genuine reading frame. The cDNA sequence for the light chain is presented in FIG. 2, and the corresponding amino acid sequence is presented in FIG. 3. The cDNA sequence of the heavy chain is presented in FIG. 4, and the corresponding amino acid sequence is presented in FIG. 5. The variable, constant, and CDR regions of the light chain are presented in FIG. 6, and the variable, constant, and CDR regions of the heavy chain are presented in FIG. 7

The DNA sequence was used as the query sequence to search the National Center for Biotechnology Information (NCBI) database (All GenBank+RefSeq Nucleotides+EMBL+DDBJ+PDB sequences). The BLAST search returned up to 15 database entries with nucleotide sequence similarity to the query sequence of NPC-1. None of the DNA sequences were identical to the NPC-1 DNA sequence, demonstrating the uniqueness of the NPC-1 monoclonal antibody described herein.

Example 5

Specific Cell Binding of NPC-1

The NPC-1 mAb produced by the hybridoma was purified by affinity chromatography using protein L-agarose matrix. The purified NPC-1 was characterized by indirect immunofluorescence as well-known in the art using various tumor cells as identified in Table 1, below. All of the tumor cell lines were obtained from the ATCC. Cells were incubated with purified NPC-1 diluted in phosphate buffered saline (PBS) for 1 hour at 4° C. The cells were washed and incubated with a fluorescein-labelled goat anti-mouse immunoglobulin antibody. The cells were then washed three times with PBS and examined by flow cytometry using a Becton-Dickinson FACScalibur and CellQuest analysis software. The results appear in Table 1 (FACS data). The data demonstrate the specific binding of NPC-1 to colorectal and pancreatic tumor cell lines, but not to ovarian or breast tumor cell lines.

TABLE 1

Cancer cell types recognized by NPC-1

| | % Cell Staining | | |
|---|---|---|---|
| Tumor Cell Line | Unstained | Isotype Control | NPC-1 |
| GEO Colorectal | 1.36 | 0.78 | 86.87 |
| LS174T Colorectal | 1.31 | 0.93 | 57.04 |
| CFPAC-1 Pancreatic | 1.24 | 0.44 | 54.65 |
| OVCAR-3 Ovarian | 0.21 | 0.19 | 0.19 |
| MCF-7 Breast | 1.23 | 0.94 | 0.19 |

Flow cytometry antibody binding data with various cultured tumor cell lines. Cells stained with 2.5 µg NPC-1 per 100,000 cells.

Example 6

ADCC Activity of NPC-1 Demonstrating Anti-Tumor Cytotoxicity

A therapeutically useful monoclonal antibody, specific for an immunogenic tumor antigen, may have one or more of the following properties: (a) high tumor tissue specificity; (b) absence of cross-reactivity to normal human tissue; and (c) a biological activity associated with destruction of tumors, such as antibody-dependent cellular cytotoxicity (ADCC). The ADCC activity of NPC-1 was tested on colon LS174T and pancreatic CFPAC-1 carcinoma lines as target cells. The ovarian cell line, OVCAR-3, served as a specificity control. ADCC was assayed using a conventional 4 hour Indium-111 release assay using normal human PBMC as effector cells, and the results are shown as the percent isotope release (% lysis) in Table 2 (ADCC data).

TABLE 2

ADCC activity of NPC-1 with various tumor cell lines.

| | | % Specific Killing (± SD) | |
|---|---|---|---|
| Tumor Cell Line | Effector:Target Cell Ratio | No mAb | NPC-1 |
| LS174T Colorectal | 50:1 | 3.2 ± 0.4 | 18.8 ± 0.5 |
| | 25:1 | 2.4 ± 0.1 | 16.2 ± 1.9 |
| | 12.5:1 | 1.4 ± 0.7 | 15.1 ± 3.3 |
| CFPAC-1 Pancreatic | 50:1 | 1.9 ± 0.8 | 10.1 ± 1.2 |
| | 25:1 | −0.6 ± 1.0 | 8.1 ± 0.9 |
| | 12.5:1 | −1.1 ± 0.4 | 3.8 ± 0.9 |
| OVCAR-3 Ovarian | 100:1 | 2.4 ± 0.4 | −1.5 ± 0.7 |
| | 50:1 | −0.1 ± 0.8 | −0.8 ± 1.0 |
| | 25:1 | 0.5 ± 0.5 | 0.0 ± 0.3 |
| | 12.5:1 | 0.4 ± 0.5 | −0.4 ± 0.1 |

Antibody-dependent cell cytotoxicity assay with various tumor cell lines. Assay was performed with 5 µg NPC-1 antibody per well.

Example 7

SDS Polyacrylamide Gel Electrophoresis Analysis of NPC-1

The native configuration of murine immunoglobulin gamma (IgG1) is comprised of four polypeptides, with two polypeptides each of a heavy chain and a light chain. One heavy chain (55 kilodaltons) is associated with one light chain (25-29 kilodaltons) and this dimer is linked to an identical dimer through disulfide bonding to complete the functional tetrameric macromolecule. The IgG molecule can be dissociated into its component heavy and light chains and separated by size on polyacrylamide gel matrix in the presence of denaturing reagent (SDS, sodium dodecyl sulfate) and an agent to reduce the disulfide bridge that links the two heterodimers (DTT, dithiothreitol). Gel electrophoresis is a common analytical method used to define the molecular mass of proteinaceous materials, such as antibodies.

Purified NPC-1 was subjected to analysis by SDS polyacrylamide gel electrophoresis in the presence of reducing agent (DTT). Three micrograms of purified NPC-1 was mixed with DTT and 4× samples buffer containing SDS, glycerol, and bromophenol blue dye. The mixture was heated to 95° C. for 2 minutes, cooled on ice, then loaded onto an SDS gradient polyacrylamide gel (4%-20% gradient) and subjected to an electric current to separate the molecular species in the NPC-1 preparation. Following electrophoresis, the gel was stained with Coomassie Blue dye to visualize the proteins on the gel, destained with water, and dried between pourous plastic sheets. The data (not shown) revealed two protein bands of molecular mass 55 kilodaltons, representing the heavy chain, and 28 kilodaltons, representing the light chain molecular species, respectively. These data show that the purified material correspond to the known molecular sizes for murine IgG1.

Example 8

Pre-Clinical Anti-Tumor Efficacy Study Design Using Chimerized NPC-1 (NPC-1Chi) Antibody Athymic nude mice, aged 4-6 month old, are used in this study. LS174T colorectal tumor cells and AsPC-1 human pancreatic tumor cells are used as the tumor models. The tumors are established by implanting 2e6 tumor cells subcutaneously on the flank of mice. Solid tumors grow to approximately 200 mm3 in 10-14 days, at which time the mice are recaged and randomized into study groups of 10 (n=10). Mice are injected intraperitoneally with NPC-1Chi and human effector cells (PBMC) every 3 days for a total of 3 cycles of injections. The mice are inspected daily for general health, and the tumors are measured with a digital caliper twice a week for approximately 28-40 days. Control mice with tumor volumes greater than 2000 mm3 are sacrificed by CO2 inhalation or cervical dislocation according to local IACUC guidelines. Tumor growth is plotted and statistical analysis is performed using ANOVA.

Experimental Groups:

| Group | Number | Tumor | Antibody | Dose (ug) | Effector Cells |
|---|---|---|---|---|---|
| 1 | 10 | LS174T | Human IgG | 400 | None |
| 2 | 10 | LS174T | Human IgG | 400 | Human PBMC |
| 3 | 10 | LS174T | NPC-1Chi | 400 | None |
| 4 | 10 | LS174T | NPC-1Chi | 400 | Human PBMC |
| 5 | 10 | AsPC-1 | Human IgG | 400 | None |
| 6 | 10 | AsPC-1 | Human IgG | 400 | Human PBMC |
| 7 | 10 | AsPC-1 | NPC-1Chi | 400 | None |
| 8 | 10 | AsPC-1 | NPC-1Chi | 400 | Human PBMC |

Example 9

Pre-Clinical Pharmacology-Toxicity Study Design Using Chimerized NPC-1Chi (NPC-1Chi) Antibody Two mouse strains are used in this study. The first is the athymic nude mouse bearing the subcutaneous AsPC-1 pancreatic tumor to study the drug metabolism-pharmacokinetics (DMPK) in a tumor-bearing animal and to study the localization of the antibody at the tumor site. The second model is the non-tumor-bearing normal mouse to study DMPK reactions in an immunocompetent animal. Four- to six-month old mice are used in the study. AsPC-1 pancreatic tumors are established by implanting 2e6 tumor cells subcutaneously on the flank of mice. Solid tumors grow to approximately 200 mm3 in 10-14 days, at which time mice are recaged and randomized into study groups of 8 (n=4 per group per timepoint). On study day-one, mice are bled for pre-treatment analysis of blood and serum. On study day one, all mice are injected intraperitoneally with NPC-1Chi or control IgG. In addition, tumor-bearing nude mice are injected intraperitoneally with human effector cells or saline. On study day four (72 hours post-injection), four mice per group are sacrificed for DMPK analysis. On study day eleven, the remaining four mice per group are sacrificed for DMPK analysis. The DMPK analysis includes hematology (complete blood cell count/differential), serum analysis (AST, ALT, BILI, CPK, CK, CREAT, CBA bead analysis for lymphokines), histological analysis (H&E stain of liver, spleen, pancreas, lung, kidney), and immunohistochemical analysis of NPC-1 localization and quantitation. Values are analyzed statistically among groups by t-test.

Experimental Groups:

| Group | Mice | Day | Mouse Tumor | Antibody | Dose (ug) | Effector Cells |
|---|---|---|---|---|---|---|
| 1 | 4 | 4 | Nude LS174T | Human IgG | 400 | None |
| 2 | 4 | 4 | Nude LS174T | Human IgG | 400 | Human PBMC |
| 3 | 4 | 4 | Nude LS174T | NPC-1Chi | 400 | None |
| 4 | 4 | 4 | Nude LS174T | NPC-1Chi | 400 | Human PBMC |
| 5 | 4 | 4 | BALB/c | Human IgG | 400 | None |
| 6 | 4 | 4 | BALB/c | Human IgG | 400 | Human PBMC |
| 7 | 4 | 4 | BALB/c | NPC-1Chi | 400 | None |
| 8 | 4 | 4 | BALB/c | NPC-1Chi | 400 | Human PBMC |
| 9 | 4 | 11 | Nude LS174T | Human IgG | 400 | None |
| 10 | 4 | 11 | Nude LS174T | Human IgG | 400 | Human PBMC |
| 11 | 4 | 11 | Nude LS174T | NPC-1Chi | 400 | None |
| 12 | 4 | 11 | Nude LS174T | NPC-1Chi | 400 | Human PBMC |
| 13 | 4 | 11 | BALB/c | Human IgG | 400 | None |
| 14 | 4 | 11 | BALB/c | Human IgG | 400 | Human PBMC |
| 15 | 4 | 11 | BALB/c | NPC-1Chi | 400 | None |
| 16 | 4 | 11 | BALB/c | NPC-1Chi | 400 | Human PBMC |

Example 10

Phase I Study of NPC-1

This trial with a chimeric version of mAb NPC-1 examines 3 dose levels (10 mg/M$^2$, 25 mg/M$^2$ and 50 mg/M$^2$ per week) given in cycles of 4 weekly doses. Any significant bowel toxicity is documented. All patients are monitored for blood in stool. Colonoscopy is used to investigate any bleeding, and random biopsy of the patients' colon mucosae may determine specific abnormalities.

Treatment continues for six months. Anticancer activity is monitored at all three dose levels. CPAA serum levels are monitored, and CT analysis may reveal a partial response of colon, pancreatic, lung, liver and lymph node metastases. Patient stability is monitored for one year.

Example 11

Chimerization of the Murine NPC-1 Antibody (NPC-1C)

When monoclonal antibodies are used as therapeutic agents to treat cancer patients, it is often beneficial to re-engineer the murine antibody to reduce its immunogenicity in humans: the administration of 100% murine antibodies in humans has been shown to elicit human anti-mouse antibody responses (HAMA), which severely reduce the therapeutic value of the antibody and may induce toxicity. Less immunogenic antibodies intended for use in humans may be made by replacing the majority of the murine immunoglobulin sequence with human immunoglobulin sequences, as described above. Such replacements dramatically reduce the immunogenicity and toxicity of the therapeutic agent intended for use in humans. Chimerization is one method for reducing the immunogenicity of murine antibodies and is the most conservative approach with respect to preserving the antigen recognition specificity. In the chimerization process, approximately 66% of the murine immunoglobulin sequence is replaced with human immunoglobulin framework sequences. One can select the human immunoglobulin isotype (IgG1, IgG2, etc.) with specific known activities depending on the intended use and mechanism of action of the resulting antibody. In addition, one can perform less conservative steps to graft simply the murine CDR loops onto the framework of a human immunoglobulin framework. This process is known as "CDR grafting" or "humanization". This process results in antibodies that are 90% to 95% human protein. Alternatively, one can "fully humanize" a murine antibody by even less conservative methods such as lambda phage display or specific amino acid replacement in the CDR loops of a human antibody to result in an altered antigen binding specificity.

Another benefit of re-engineering the murine antibody to be produced in a recombinant expression system is that the genes coding for the heavy and light chain molecules comprising the fully assembled antibody can be altered at this stage. One may make changes in codon usage to enhance protein expression levels in the species of cell that will be used to produce the antibodies. For example, it is known that there are differences in percent codons used for specific amino acids in hamster cells compared to human cells. Alternatively, one can introduce alternative amino acids that would result in an antibody that has different carbohydrate processing in the producer cells. Such different carbohydrate composition can alter the activities of the antibody product. In addition, the introduction of alternative amino acids in the constant regions of the antibody, or the use of different human immunoglobulin isotypes, can alter the biological activities of the final antibody product. For example, one can change the mechanism of cytotoxicity of an antibody from primarily cell-mediated cytotoxicity (ADCC) to primarily complement-mediated cytotoxicity (CDC). This represents a partial list of alterations that may be made to an antibody to enhance specific functions or expression of an antibody intended for use in humans.

The NPC-1C chimeric antibody was designed to include the variable regions of the heavy and light chains of murine NPC-1 linked to the human immunoglobulin gamma-1 and kappa constant regions, respectively. A mammalian expression vector containing the murine dihydrofolate reductase (dhfr) gene (Biofactura, Rockville, Md.) utilizes the hCMV promoter/enhancer region to efficiently transcribe the light and heavy chain genes and the dhfr gene as a selectable marker (pBF-dhfr). This vector provides a high level of antibody production in Chinese Hamster Ovary (CHO) cells. The genes encoding the murine sequence for NPC-1 heavy and light chains linked to the human constant regions were chemically synthesized using codon sequences optimized for CHO cells and containing the correct restriction enzyme sites at the 5' and 3' ends for simple and direct cloning into the pBF-dhfr mammalian expression vector. The genes were provided in pUC shuttle plasmids following sequence verification.

A two-step process was used to construct the dual gene vector containing both the heavy and light chain genes encoding NPC-1. Each chain was cloned separately into the pBF-dhfr vector. The NPC-1 chi heavy chain was ligated into the KpnI site of the pBF-dhfr vector, generating Clone 19 in the appropriate reading frame. NPC-1chi LC containing BglII ends was ligated into the BamHI site of pBF-dhfr vector generating clone 1 in the appropriate reading frame. Clone 1 DNA was used to PCR amplify an NPC-1 LC cassette containing BglII ends and the hCMV promoter and NPC-1 chi LC. The following primers were utilized for the amplification of NPC-1chi LC cassette containing BglII ends: 5' CMV cassette primer: 5'GTC ACT AGA TCT GCC GTT GAC ATT GAT TAT TGA C 3' (SEQ ID NO:13) and 3' BGHpA cassette primer: 5' ACA CTG AGA TCT TCC CCA GCA TGC CTG CTA TTG TCT T 3' (SEQ ID NO:14) using Invitrogen's AccuPrime Pfx DNA polymerase according to manufacturer's instructions. Briefly, the template, 200 ng of Clone 1 DNA was denatured for 2 min. at 95° C. (Hot Start), followed by thirty cycles of 94° C. for 15 sec., 55° C. for 30 sec., and 68° C. for 2 min. The PCR product was analyzed and cut out of a 1% Agarose TAE gel, eluted with a QIAquick gel elution system (Qiagen) and the ends cut with BglII.

The gel purified fragment was ligated into BglII cut clone 19 containing the heavy chain. Chemically competent DH5alpha *E. coli* cells were transformed with the ligated DNA and colonies screened with NdeI. Clones with a small NdeI fragment (0.75 kb) contained a construct with opposing LC and HC cassettes. A large NdeI fragment (1.9 kb) contained a construct with LC and HC cassettes in tandem. Six clones of each type were used to transfect human 293T cells with Lipofectamine-2000 (Invitrogen).

Example 12

Expression and Purification of NPC-1C

The chimerized antibody NPC-1C was cloned into a mammalian expression plasmid DNA designated pBF-dhfr.

The resulting DNA was named NPC-1C-pBF-dhfr. Two clones were selected, 13-0 (opposing orientation) and 9T (tandem orientation) for the development of an antibody producing stable CHO cell line. The plasmids were grown in LB-ampicillin (1 liter) and purified by CsCl ultracentrifugation (2×) and transfected into CHO-DG44 cells using Lipofectamine 2000 (Invitrogen). Stable NPC-1C expressing CHO cell lines were developed by an amplification procedure by increasing the Methotrexate concentrations. Clones expressing high levels of functional antibody were selected and grown.

The NPC-1C antibody was purified from culture medium following transfection of either CHO cells or 293T cells. The antibody was used for characterization the biological functions of the chimeric antibody. Cell culture medium was collected following 4 days of incubation from the time of transfection with the expression plasmid. The medium was diluted with 10×PBS to yield a final 1× concentration of PBS to adjust the salt concentration and pH of the medium for efficient binding to protein A. The medium was applied to a protein A-Sepharose resin in a glass column. The resin was washed extensively with PBS, then the bound antibody was eluted with 0.1M glycine pH 3.0 and the fractions containing the protein peak were pooled and dialyzed extensively against PBS pH 7.4. The purified chimeric antibody was stored at 4° for later characterization and testing.

The purified NPC-1C antibody was characterized by standard gel electrophoresis on a 4% to 20% gradient SDS-polyacrylamide gel. The antibody was run under both non-reducing and reducing conditions to evaluate the amount of intact, fully assembled tetrameric antibody (150 kD, representing $H_2L_2$) versus the amount of heavy chain (50 kD) and light chain (25 kD) proteins expressed in the recombinant expression system from the NPC-1C-pBF-dhfr plasmid.

Example 13

Tumor Cell Binding Specificity of NPC-1C

The chimeric NPC-1C mAb produced by transient transfection of 293T cells was purified by affinity chromatography using protein A-Sepharose matrix. The purified NPC-1C was characterized by indirect immunofluorescence, using various tumor cells listed in Table 3 below. All of the tumor cell lines were obtained from the ATCC. Cells were incubated with purified NPC-1C diluted in phosphate buffered saline (PBS) for 1 hour at 4° C. The cells were washed and incubated with a fluorescein-labelled goat anti-human immunoglobulin antibody. The cells were then washed with PBS and examined by flow cytometry using a Becton-Dickinson FACScalibur and CellQuest analysis software. The results appear in Table 3 (FACS data). The data demonstrate the selective binding of NPC-1C to some colorectal and pancreatic tumor cell lines, but not to squamous or prostate tumor cell lines. It should be noted that the data in Table 3 were generated with approximately 16-fold lower antibody concentration than is typically tested in this assay format. Thus, the percent of calls that stained positively and the intensity of the staining (mean fluorescence intensity, mfi) are reported here using a sub-optimal amount of the NPC-1C antibody which may under-report the actual cell binding potential of the antibody in a typical cell binding experiments using an optimized antibody concentration.

TABLE 3

Cell binding activity of NPC-1C antibody

| Tumor Cell Line | % Cell Staining (mfi) | | |
|---|---|---|---|
| | FITC-Ab only | NPC-1Chi (prep 1) | NPC-1Chi (prep 2) |
| LS174T Colorectal | 1.26 (19) | 11.59 (43) | 11.22 (47) |
| SW480 Colorectal | 0.69 (26) | 1.41 (44) | 1.34 (64) |
| SW620 Colorectal | 0.52 (101) | 0.24 (184) | 0.85 (74) |
| SW1463 Colorectal | 0.95 (37) | 3.72 (410) | 4.29 (399) |
| SW1116 Colorectal | 1.13 (54) | 1.12 (97) | 2.37 (174) |
| HT-29 Colorectal | 1.14 (63) | 1.30 (55) | 1.09 (34) |
| Colo-205 Colorectal | 0.65 (28) | 2.26 (154) | 1.44 (67) |
| CFPAC-1 Pancreatic | 1.20 (17) | 11.23 (16) | 10.55 (15) |
| AsPC-1 Pancreatic | 0.04 (29) | 0.43 (33) | 0.35 (34) |
| Panc-1 Pancreatic | 1.04 (14) | 0.75 (69) | 0.41 (31) |
| H520 Squamous | 1.48 (64) | 1.66 (129) | 0.93 (173) |
| H226 Squamous | 1.39 (38) | 0.49 (32) | 0.40 (32) |
| HTB-35 Squamous | 3.96 (37) | 4.83 (97) | 3.85 (123) |
| SW756 Squamous | 1.63 (117) | 0.75 (186) | 2.14 (178) |
| PC-3 Prostate | 1.49 (11) | 1.34 (17) | 1.52 (28) |
| DU145 Prostate | 0.41 (69) | 0.24 (17) | 0.14 (277) |

Flow cytometric antibody binding data with various cultured tumor cell lines. Cells stained with 2 µg NPC-1C per 100,000 cells.

Example 14

ADCC Activity of NPC-1C Demonstrating Anti-Tumor Cytotoxicity

A therapeutically useful mAb, specific for an immunogenic tumor antigen, should have one or more of the following properties: (a) high tumor tissue specificity, (b) absence of cross-reactivity to normal human tissue, and (c) a biological activity associated with destruction of tumors, such as antibody-dependent cellular cytotoxicity (ADCC). The ADCC activity of NPC-1C was tested on colon and pancreatic carcinoma lines as target cells. Melanoma and prostate tumor cell lines were included as a specificity controls. ADCC was assayed using a conventional four-hour $^{111}$Indium release assay using normal activated human PBMC as effector cells, and the results are shown as the percent specific isotope release (% lysis) in Table 4 (ADCC data). The data demonstrate robust in vitro killing of colorectal and pancreatic tumor cell lines mediated specifically by the NPC-1C antibody. In contrast, no cytotoxicity was measured against the melanoma or prostate tumor line controls tested in the assay, demonstrating specific NPC-1C-dependent recognition and killing of colorectal and pancreatic tumor cells. It should be noted that the data in Table 4 were generated with approximately 16-fold lower antibody concentration than is typically tested in this assay format. Although robust and specific cytotoxicity was observed using a sub-optimal concentration of NPC-1C, these data may under-report the actual cytotoxic potential of the antibody in a typical ADCC experiment using an optimized antibody concentration.

TABLE 4

ADCC activity of NPC-1C antibody.

| Tumor Cell Line | Effector:Target Cell Ratio | % Specific Killing (± SEM) | |
|---|---|---|---|
| | | Isotype control Ab | NPC-1C |
| Colo-205 (Colorectal) | 50:1 | 9.8 ± 1.9 | 66.7 ± 0.6 |
| | 25:1 | 0.8 ± 1.2 | 46.4 ± 1.6 |
| | 12.5:1 | −0.5 ± 0.1 | 32.8 ± 2.0 |

TABLE 4-continued

ADCC activity of NPC-1C antibody.

| Tumor Cell Line | Effector:Target Cell Ratio | % Specific Killing (± SEM) | |
|---|---|---|---|
| | | Isotype control Ab | NPC-1C |
| SW620 (Colorectal) | 50:1 | 1.6 ± 0.2 | 63.7 ± 2.9 |
| | 25:1 | 3.5 ± 1.8 | 61.0 ± 1.8 |
| | 12.5:1 | 0.0 ± 0.3 | 51.5 ± 0.9 |
| SW1463 (Colorectal) | 50:1 | 0.1 ± 1.1 | 33.8 ± 1.0 |
| | 25:1 | −1.3 ± 0.2 | 25.5 ± 0.6 |
| | 12.5:1 | −1.2 ± 0.1 | 17.9 ± 1.7 |
| LS174T (Colorectal) | 50:1 | −1.2 ± 0.1 | 26.8 ± 2.9 |
| | 25:1 | −0.8 ± 0.1 | 18.5 ± 4.1 |
| | 12.5:1 | −1.1 ± 0.0 | 9.5 ± 0.5 |
| AsPC-1 (Pancreatic) | 50:1 | −0.8 ± 2.9 | 44.5 ± 6.8 |
| | 25:1 | −7.0 ± 2.2 | 36.2 ± 2.6 |
| | 12.5:1 | −1.2 ± 0.9 | 26.5 ± 6.7 |
| CFPAC-1 (Pancreatic) | 50:1 | −1.2 ± 2.3 | 26.9 ± 1.6 |
| | 25:1 | −2.4 ± 0.1 | 23.2 ± 2.2 |
| | 12.5:1 | −2.0 ± 0.4 | 11.1 ± 1.6 |
| PANC-1 (Pancreatic) | 50:1 | −2.2 ± 0.4 | 46.8 ± 2.1 |
| | 25:1 | −2.5 ± 0.4 | 33.2 ± 3.3 |
| | 12.5:1 | −3.9 ± 0.3 | 21.2 ± 0.6 |
| SK-MEL (Melanoma) | 50:1 | 2.7 ± 0.7 | 4.6 ± 1.1 |
| | 25:1 | 1.5 ± 0.3 | 3.3 ± 1.1 |
| | 12.5:1 | 1.6 ± 0.4 | 2.3 ± 0.6 |
| DU145 (Prostate) | 50:1 | −0.3 ± 0.2 | −0.5 ± 0.3 |
| | 25:1 | −0.7 ± 0.1 | 0.3 ± 0.8 |
| | 12.5:1 | −0.2 ± 0.2 | −0.3 ± 0.1 |

Antibody-dependent cell cytotoxicity assay with various tumor cell lines. Assay was performed with 250 ng NPC-1C per well.

Example 15

Immunohistochemical Staining of Human Tissues by NPC-1C Demonstrating Specific Cancer Cell Binding The NPC-1C antibody was tested for its ability to specifically stain a number of human tissues to demonstrate its utility as a cancer diagnostic and monitoring antibody. These tissues were tested as both collections of microarrays containing multiple samples, and as individual biopsy tissue sections, both frozen and in paraffin blocks. Immunohistochemical staining can reveal the applicability of the antibody as a useful research or commercial product.

The purified NPC-1C antibody was first biotinylated using a commercial kit (Roche) to control for background staining that is known to occur when using a human antibody to stain human tissues. The biotinylated NPC-1C antibody was tested at 5 µg/mL diluted in PBS buffer against tissue sections and tissue arrays slides from Accurate Chemical Co. (Westbury, N.Y.). Paraffin tissues were first de-paraffinized. Frozen tissues were thawed and washed in PBS. Paraffin tissues were incubated with Peroxo Block (Zymed, San Fracisco, Calif.) for 1.5 min. Frozen tissues were incubated with Peroxo Block (Zymed) for 30 sec. Both samples were rinsed 3× in PBS, then incubated with avidin for 10 min. (Zymed), and rinsed 3× with PBS. Samples were then incubated with CAS Block for 10 min. (Zymed) and shaken off the sample (no washing). The NPC-1C was incubated with the tissues for 1 hour, then rinsed off 3× with PBS. Streptavidin/HRP (Dako, Carpinteria, Calif.) was applied at a 1:400 dilution for 30 min., then washed 3× with PBS. The DAB substrate (Zymed) was added for 1 min, then washed 3× with PBS. Samples were then counterstained with hematoxylin for 3 min then rinsed and mounted on glass slides for analysis under a light microscope. Samples were scored for the number and intensity of immunostaining specifically with the NPC-1C antibody. Samples were scored with a 0-1-2-3 system which reflects both the number of cells that stain positive in the section and the intensity of the brown stain per cell.

The samples tested were tissues independently diagnosed by a pathologist as colon cancer, normal colon, pancreatic cancer, normal pancreas, or cancer of the uterus or prostate. The data from the immunohistochemical staining with NPC-1C is shown in Table 5 below. The data demonstrate that the NPC-1C antibody stains tissues from both colon cancers (43% of all samples tested, n=48) and pancreatic cancers (32% of all samples, n=11), whereas NPC-1C does not cross-react with normal pancreas and cross-reacted with only 25% of normal colon tissues tested. When NPC-1C was tested for staining against other cancer types, it showed some immunoreactivity with an antigen expressed on uterine cancer samples (24%, n=42) but not normal uterus tissue, and 24% of prostate cancer samples (n=40) but not with normal prostate samples. The data show a selective binding specificity of NPC-1C for colon and pancreatic cancer tissues, with some reactivity to uterine and prostate cancer tissues. There was no cross-reactivity, however, of NPC-1C with normal tissues from pancreas, uterus or prostate, and a minor fraction of normal colon tissues.

TABLE 5

Immunohistochemical staining of human tissue samples with NPC-1C

| Human tissue sample | Tissue staining intensity | | | | | |
|---|---|---|---|---|---|---|
| | Negative | Weak | +1 | +2 | +3 | +4 |
| Colon cancer | 27/48 | 5/48 | 7/48 | 4/48 | | 5/48 |
| (Accumax array) | (56%) | (10%) | (15%) | (8%) | | (10%) |
| Normal colon | 3/4 | | | 1/4 | | |
| (Accumax array) | (75%) | | | (25%) | | |
| Pancreas cancer | 7/11 | | | 4/11 | | |
| (CHTN) | (64%) | | | (32%) | | |
| Normal pancreas | 3/3 | | | | | |
| (CHTN) | (100%) | | | | | |
| Uterus cancer | 32/42 | | | 2/42 | 8/42 | |
| (Accumax array) | (76%) | | | (5%) | (19%) | |
| Normal uterus | 12/12 | | | | | |
| (Accumax array) | (100%) | | | | | |

TABLE 5-continued

Immunohistochemical staining of human tissue samples with NPC-1C

| Human tissue sample | Tissue staining intensity | | | | | |
|---|---|---|---|---|---|---|
| | Negative | Weak | +1 | +2 | +3 | +4 |
| Prostate cancer (Accumax array) | 30/40 (75%) | | 5/40 (12%) | 5/40 (12%) | | |
| Normal prostate (Accumax array) | 4/4 (100%) | | | | | |

Having now fully described this invention, it will be appreciated by those skilled in the art that the same can be performed within a wide range of equivalent parameters, concentrations, and conditions without departing from the spirit and scope of the invention and without undue experimentation.

Although this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A monoclonal antibody, or antigen-binding fragment thereof, that binds to a human colorectal and pancreatic carcinoma-associated antigen (CPAA), wherein said monoclonal antibody or antigen-binding region thereof comprises the light chain CDR1 amino acid sequence of SEQ ID NO:7, light chain CDR2 amino acid sequence of SEQ ID NO:8, and light chain CDR3 amino acid sequence of SEQ ID NO:9, and wherein said monoclonal antibody or antigen-binding region thereof comprises the heavy chain CDR1 amino acid sequence of SEQ ID NO:10, heavy chain CDR2 amino acid sequence of SEQ ID NO:11, and heavy chain CDR3 amino acid sequence of SEQ ID NO:12.

2. The monoclonal antibody, or antigen-binding fragment thereof, of claim 1, wherein the light chain of said antibody: (a) is encoded by the nucleic acid sequence of SEQ ID NO: 1 or SEQ ID NO: 2; or (b) comprises the amino acid sequence of SEQ ID NO: 3.

3. The monoclonal antibody, or antigen-binding fragment thereof, of claim 1, wherein the heavy chain of said antibody: (a) is encoded by the nucleic acid sequence of SEQ ID NO: 4 or SEQ ID NO: 5; or (b) comprises the amino acid sequence of SEQ ID NO: 6.

4. The monoclonal antibody, or antigen-binding fragment thereof, of claim 1, wherein the light chain of said antibody comprises the amino acid sequence of SEQ ID NO: 3 and the heavy chain of said antibody comprises the amino acid sequence of SEQ ID NO: 6.

5. The monoclonal antibody, or antigen-binding fragment thereof, of claim 1, wherein the light chain of said antibody is encoded by the nucleic acid sequence of SEQ ID NO: 1 or SEQ ID NO: 2 and the heavy chain of said antibody is encoded by the nucleic acid sequence of SEQ ID NO: 4 or SEQ ID NO: 5; or (b) comprises the amino acid sequence of SEQ ID NO: 6.

6. The monoclonal antibody, or antigen-binding fragment thereof, of claim 1, wherein said antibody is a chimeric, humanized, or bifunctional antibody.

7. The monoclonal antibody, or antigen-binding fragment thereof, of claim 1, wherein said antibody comprises a humanized heavy chain and comprises a humanized light chain.

8. The monoclonal antibody, or antigen-binding fragment thereof, of claim 7, wherein said fragment is a Fab, Fab', F(ab')2, Fv, or a portion of the antibody that is capable of binding said antigen.

9. The monoclonal antibody, or antigen-binding fragment thereof, of claim 7, wherein said antibody is conjugated to or administered in association with a cytotoxic agent.

10. The monoclonal antibody, or antigen-binding fragment thereof, of claim 9, wherein said cytotoxic agent comprises a moiety that inhibits DNA, a moiety that inhibits RNA synthesis, a moiety that inhibits protein synthesis, a radionuclide, ribosomal inhibiting protein, $^{212}$Bi, $^{131}$I, $^{188}$Re, $^{90}$Y, vindesine, methotrexate, adriamycin, cisplatin, pokeweed antiviral protein, Pseudomonas exotoxin A, ricin, diphtheria toxin, ricin A chain, or a cytotoxic phospholipase enzyme.

11. The monoclonal antibody, or antigen-binding fragment thereof, of claim 1, wherein said antibody is a chimeric antibody comprising human immunoglobulin gamma-1 and kappa constant regions.

12. The monoclonal antibody, or antigen-binding fragment thereof, of claim 1, wherein the antibody comprises a human IgA, IgM, or IgA constant region.

13. The monoclonal antibody, or antigen-binding fragment thereof, of claim 1, wherein the antibody comprises a human IgG1, IgG2, IgG3, or IgG4 constant region.

14. The monoclonal antibody, or antigen-binding fragment thereof, of claim 1, wherein said CPAA is an antigen bound by a NPC-1 monoclonal antibody.

15. A composition for treating pancreatic carcinoma comprising a therapeutically effective amount of a monoclonal antibody, or antigen-binding fragment thereof, of claim 1.

16. The composition of claim 15, which is formulated for administration to a subject that has or is suspected of having pancreatic cancer, is a disease-free individual, or does not exhibit symptoms of disease.

17. The composition of claim 16, further comprising at least one chemotherapeutic agent.

18. The composition of claim 17, wherein said at least one chemotherapeutic agent comprises another antibody, a lymphokine, or a hemopoietic growth factor.

* * * * *

SEQUENCE LISTING

```
<160> NUMBER OF SEQ ID NOS: 14

<210> SEQ ID NO 1
<211> LENGTH: 965
<212> TYPE: DNA
<213> ORGANISM: Murinae gen. sp.

<400> SEQUENCE: 1
atgagaatac cattaattag ctagggacca aaattcaaag acaaaatgga ttttcaggtg      60
cagattttca gcttcctgct aatcagtgcc tcagtcatac tgtccagagg acaagttgtt     120
ctcacccagt ctccagtaat catgtctgca tctccagggg agaaggtcac catgacctgc     180
agtgccagct caagtataag ttacatgtac tggtaccagc agaagccagg cacctccccc     240
aaaagatgga tttatgacac atccaaactg gcttctggag tccctgctcg cttcagtggc     300
agtgggtctg ggacctctta ttctctcaca atcagcaaca tggaggctgg agatgctgcc     360
acttattact gccatcagcg ggattcttac ccatggacgt tcggtggagg caccaacctg     420
gaaatcaaac gggctgatgc tgcaccaact gtatccatct tcccaccatc cagtgagcag     480
ttaacatctg gaggtgcctc agtcgtgtgc ttcttgaaca acttctaccc caaagacatc     540
aatgtcaagt ggaagattga tggcagtgaa cgacaaaatg gcgtcctgaa cagttggact     600
gatcaggaca gcaaagacag cacctacagc atgagcagca ccctcacgtt gaccaaggac     660
gagtatgaac gacataacag ctatacctgt gaggccactc acaagacatc aacttcaccc     720
attgtcaaga gcttcaacag gaatgagtgt tagagacaaa ggtcctgaga cgccaccacc     780
agctccccag ctccatccta tcttcccttc taaggtcttg gaggcttccc cacaagcgac     840
ctaccactgt tgcggtgctc caaacctcct ccccacctcc ttctcctcct cctcccttc      900 cttggctttt atcatgctaa tatttgcaga aaatattcaa taaagtgagt ctttgcactt     960
gaaaa                                                                 965

<210> SEQ ID NO 2
<211> LENGTH: 965
<212> TYPE: RNA
<213> ORGANISM: Murinae gen. sp.

<400> SEQUENCE: 2
augagaauac cauuaauuag cuagggacca aaauucaaag acaaaaugga uuuucaggug      60
```

```
cagauuuuca gcuuccugcu aaucagugcc ucagucauac uguccagagg acaaguuguu      120
cucacccagu uccaguaau caugucugca ucuccagggg agaaggucac caugaccugc       180
agugccagcu caaguauaag uuacauguac ugguaccagc agaagccagg caccuccccc      240
aaaagaugga uuuaugacac auccaaacug gcuucuggag ucccugcucg uucagugge       300 agugggucug ggaccucuua uucucucaca aucagcaaca uggaggcugg agaugcugcc      360
acuuauuacu gccaucagcg ggauucuuac ccauggacgu ucgguggagg caccaaccug      420
gaaaucaaac gggcugaugc ugccaaccu guaccaucu ucccaccauc cagugagcag        480
uuaacaucug gaggugccuc agucgugugc uucuugaaca acuucuaccc caaagacauc      540
aaugucaagu ggaagauuga uggcagugaa cgacaaaaug gcguccugaa caguuggacu      600
gaucaggaca gcaaagacag caccuacagc augagcagca cccucacguu gaccaaggac      660
gaguaugaac gacauaacag cuauaccugu gaggccacuc acaagacauc aacuucaccc      720
auugucaaga gcuucaacag gaaugagugu uagagacaaa gguccugaga cgccaccacc      780
agcuccccag cuccauccua ucuucccuuc uaaggucuug gaggcuuccc cacaagcgac      840
cuaccacugu ugcggugcuc caaaccuccu ccccaccucc uucuccccu ccucccuuuc       900 cuuggcuuuu aucaugcuaa uauuugcaga aaauauucaa uaaagugagu cuuugcacuu      960
gaaaa                                                                 965

<210> SEQ ID NO 3
<211> LENGTH: 226
<212> TYPE: PRT
<213> ORGANISM: Murinae gen. sp.

<400> SEQUENCE: 3

Met Asp Phe Gln Val Gln Ile Phe Ser Phe Leu Leu Ile Ser Ala Ser
1               5                   10                  15

Val Ile Leu Ser Arg Gly Gln Val Val Leu Thr Gln Ser Pro Val Ile
                20                  25                  30

Met Ser Ala Ser Pro Gly Glu Lys Val Thr Met Thr Cys Ser Ala Ser
            35                  40                  45

Ser Ser Ile Ser Tyr Met Tyr Trp Tyr Gln Gln Lys Pro Gly Thr Ser
        50                  55                  60

Pro Arg Trp Ile Tyr Asp Thr Ser Lys Leu Ala Ser Gly Val Pro Ala
65                  70                  75                  80

Arg Phe Ser Gly Gly Ser Gly Thr Ser Tyr Ser Leu Thr Ile Ser Asn
                85                  90                  95

Met Glu Ala Gly Asp Ala Ala Tyr Tyr Cys His Gln Arg Asp Ser Tyr
            100                 105                 110

Pro Trp Thr Phe Gly Gly Gly Thr Asn Leu Ile Lys Arg Ala Asp Ala
        115                 120                 125

Ala Pro Thr Val Ser Ile Phe Pro Pro Ser Ser Glu Gln Thr Ser Gly
130                 135                 140

Gly Ala Ser Val Val Cys Phe Leu Asn Asn Phe Tyr Pro Lys Asp Ile
145                 150                 155                 160

Val Lys Trp Lys Ile Asp Gly Ser Glu Arg Gln Asn Gly Val Leu Asn
                165                 170                 175

Ser Trp Thr Gln Asp Ser Lys Asp Ser Thr Tyr Ser Met Ser Ser Thr
            180                 185                 190

Leu Thr Leu Thr Lys Asp Tyr Glu Arg His Asn Ser Tyr Thr Cys Glu
        195                 200                 205
```

```
        Ala Thr His Lys Thr Ser Thr Ser Pro Val Lys Ser Phe Asn Arg Asn
            210                 215                 220

Glu Cys
        225

<210> SEQ ID NO 4
<211> LENGTH: 1523
<212> TYPE: DNA
<213> ORGANISM: Murinae gen. sp.

<400> SEQUENCE: 4
ttttccatcc tcttctcata gagcctccat cagaccatgg ctgtcctggc actgctcctc      60
tgcctggtga cattcccaag ctgtgtcctg tcccaggtgc agctgaagga gtcaggacct     120
gacctggtgg cgccctcaca gagcctgtcc atcacatgca ctgtctcagg attctcatta     180
agcaaatttg gtgtaaactg ggttcgccag cctccaggaa agggtctgga gtggctggga     240
gtaatatggg gtgacgggag cacaagttat aattcaggtc tcatatcaag actgagcatc     300
agcaaggaga actccaagag ccaggttttc ttaaaactga cagtctgca agctgatgac     360 acagccacat actactgtgt caaaccgggg ggtgactact ggggtcacgg aacctcagtc     420
accgtctcct cagccaaaac gacaccccca tctgtctatc cactggcccc tggatctgct     480
gcccaaacta actccatggt gaccctggga tgcctggtca agggctattt ccctgagcca     540
gtgacagtga cctggaactc tggatccctg tccagcggtg tgcacacctt cccagctgtc     600
ctgcagtctg acctctacac tctgagcagc tcagtgactg tcccctccag cacctggccc     660
agcgagaccg tcacctgcaa cgttgcccac ccggccagca gcaccaaggt ggacaagaaa     720
attgtgccca gggattgtgg ttgtaagcct tgcatatgta cagtcccaga agtatcatct     780
gtcttcatct tcccccccaaa gcccaaggat gtgctcacca ttactctgac tcctaaggtc     840
acgtgtgttg tggtagacat cagcaaggat gatcccgagg tccagttcag ctggtttgta     900
gatgatgtgg aggtgcacac agctcagacg caaccccggg aggagcagtt caacagcact     960
ttccgctcag tcagtgaact tcccatcatg caccaggact ggctcaatgg caaggagttc    1020
aaatgcaggg tcaacagtgc agcttttcct gcccccatcg agaaaaccat ctccaaaacc    1080
aaaggcagac cgaaggctcc acaggtgtac accattccac ctcccaagga gcagatggcc    1140
aaggataaag tcagtctgac ctgcatgata acagacttct tccctgaaga cattactgtg    1200
gagtggcagt ggaatgggca gccagcggag aactacaaga cactcagcc catcatggac    1260 acagatggct cttacttcgt ctacagcaag ctcaatgtgc agaagagcaa ctgggaggca    1320
ggaaatactt tcacctgctc tgtgttacat gagggcctgc acaaccacca tactgagaag    1380
agcctctccc actctcctgg taaatgatcc cagtgtcctt ggagccctct ggtcctacag    1440
gactctgaca cctacctcca cccctccctg tataaataaa gcacccagca ctgccttggg    1500
accctgcaaa aaaaaaaaaa aaa                                            1523

<210> SEQ ID NO 5
<211> LENGTH: 1523
<212> TYPE: RNA
<213> ORGANISM: Murinae gen. sp.

<400> SEQUENCE: 5
uuuuccaucc ucuucucaua gagccuccau cagaccaugg cuguccuggc acugcuccuc      60
ugccugguga cauucccaag cuguguccug ucccaggugc agcugaagga gucaggaccu     120
```

| | |
|---|---|
| gaccugguggcgcccucacagagccugucc aucacaugca cugucucagg auucucauua | 180 |
| agcaaauuug guguaaacug gguucgccag ccuccaggaa agggucugga guggcuggga | 240 |
| guauaugggg ugacgggag cacaaguuau aauucagguc ucauaucaag acugagcauc | 300 |
| agcaaggaga acuccaagag ccagguuuuc uuaaaacuga acagucugca agcugaugac | 360 |
| acagccacau acuacugugu caaaccgggg ggugacuacu ggggucacgg aaccucaguc | 420 |
| accgucuccu cagccaaaac gacaccccca ucugucuauc cacuggcccc uggaucugcu | 480 |
| gcccaaacua acuccauggu gacccuggga ugccggguca agggcuauuu cccugagcca | 540 |
| gugacaguga ccuggaacuc uggauccug ccagcggug ugcacaccuu cccagcuguc | 600 |
| cugcagucug accucuacac ucugagcagc ucagugacuu cccccuccag caccuggccc | 660 |
| agcgagaccg ucaccugcaa cguugcccac ccggccagca gcaccaaggu ggacaagaaa | 720 |
| auugugccca gggauugugg uuguaagccu ugcauaugua caguccccaga aguaucaucu | 780 |
| gucuucaucu uccccccaaa gcccaaggau gugcucacca uuacucugac uccuaagguc | 840 |
| acguguguug ugguagacau cagcaaggau gaucccgagg uccaguucag cugguuugua | 900 |
| gaugaugugg aggugcacac agcucagacg caaccccggg aggagcaguu caacagcacu | 960 |
| uuccgcucag ucagugaacu ucccaucaug caccaggacu ggcucaaugg caaggaguuc | 1020 |
| aaaugcaggg ucaacagugc agcuuucccu gcccccaucg agaaaaccau cuccaaaacc | 1080 |
| aaaggcagac cgaaggcucc acagguguac accauuccac cucccaagga gcagaauggcc | 1140 |
| aaggauaaag ucagucugac cugcaugaua acagacuucu ucccugaaga cauuacugug | 1200 |
| gaguggcagu ggaaugggca gccagcggag aacuacaaga cacucagcc caucauggac | 1260 |
| acagauggcu cuuacuucgu cuacagcaag cucaaugugc agaagagcaa cugggaggca | 1320 |
| ggaaauacuu ucaccugcuc uguguuacau gagggccugc acaaccacca uacugagaag | 1380 |
| agccucuccc acucccuggu aaaugaucc cagugccuu ggagcccucu gguccuacag | 1440 |
| gacucugaca ccuaccucca ccccucccug uauaaauaaa gcacccagca cugccuuggg | 1500 |
| acccugcaaa aaaaaaaaaa aaa | 1523 |

```
<210> SEQ ID NO 6
<211> LENGTH: 455
<212> TYPE: PRT
<213> ORGANISM: Murinae gen. sp.

<400> SEQUENCE: 6

Met Ala Val Leu Ala Leu Leu Cys Leu Val Thr Phe Pro Ser Cys
1               5                   10                  15

Val Leu Ser Gln Val Gln Leu Lys Glu Ser Gly Pro Asp Leu Val Ala
            20                  25                  30

Pro Ser Gln Ser Leu Ser Ile Thr Cys Ile Val Ser Gly Phe Ser Leu
        35                  40                  45

Ser Lys Phe Gly Val Asn Trp Val Arg Gln Pro Pro Gly Lys Gly Leu
    50                  55                  60

Glu Trp Leu Gly Val Ile Trp Gly Asp Gly Ser Thr Ser Tyr Asn Ser
65                  70                  75                  80

Gly Leu Ile Ser Arg Leu Ser Ile Lys Glu Asn Ser Lys Ser Gln Val
                85                  90                  95

Phe Leu Lys Leu Asn Ser Leu Gln Ala Asp Asp Thr Ala Thr Tyr Tyr
            100                 105                 110

Cys Val Lys Pro Gly Gly Asp Tyr Trp Gly His Gly Thr Ser Val Thr
        115                 120                 125
```

```
Val Ser Ser Ala Lys Thr Thr Pro Pro Ser Val Tyr Pro Leu Ala Pro
    130                 135                 140

Gly Ser Ala Ala Gln Thr Asn Ser Met Val Thr Leu Gly Cys Leu Val
145                 150                 155                 160

Lys Gly Tyr Phe Pro Glu Pro Val Thr Val Thr Trp Asn Ser Gly Ser
                165                 170                 175

Leu Ser Ser Gly Val His Thr Phe Pro Ala Val Leu Gln Ser Asp Leu
            180                 185                 190

Tyr Thr Leu Ser Ser Ser Val Thr Val Pro Ser Ser Thr Trp Pro Ser
        195                 200                 205

Glu Thr Val Thr Cys Asn Val Ala His Pro Ala Ser Ser Thr Lys Val
210                 215                 220

Asp Lys Lys Ile Val Pro Arg Asp Cys Gly Cys Lys Pro Cys Ile Cys
225                 230                 235                 240

Thr Val Pro Glu Val Ser Ser Val Phe Ile Phe Pro Pro Lys Pro Lys
                245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Gln Pro Arg Glu Glu Gln Phe
290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Pro Lys Glu Gln Met Ala Lys
        355                 360                 365

Asp Lys Val Ser Leu Thr Cys Met Ile Thr Asp Phe Phe Pro Glu Asp
370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys
    450                 455

<210> SEQ ID NO 7
<211> LENGTH: 10
<212> TYPE: PRT
<213> ORGANISM: Murinae gen. sp.

<400> SEQUENCE: 7

Ser Ala Ser Ser Ser Ile Ser Tyr Met Tyr
1               5                   10

<210> SEQ ID NO 8
<211> LENGTH: 7
<212> TYPE: PRT
```

-continued

```
<213> ORGANISM: Murinae gen. sp.

<400> SEQUENCE: 8

Asp Thr Ser Lys Leu Ala Ser
1               5

<210> SEQ ID NO 9
<211> LENGTH: 9
<212> TYPE: PRT
<213> ORGANISM: Murinae gen. sp.

<400> SEQUENCE: 9

His Gln Arg Asp Ser Tyr Pro Trp Thr
1               5

<210> SEQ ID NO 10
<211> LENGTH: 6
<212> TYPE: PRT
<213> ORGANISM: Murinae gen. sp.

<400> SEQUENCE: 10

Ser Lys Phe Gly Val Asn
1               5

<210> SEQ ID NO 11
<211> LENGTH: 16
<212> TYPE: PRT
<213> ORGANISM: Murinae gen. sp.

<400> SEQUENCE: 11

Val Ile Trp Gly Asp Gly Ser Thr Ser Tyr Asn Ser Gly Leu Ile Ser
1               5                   10                  15

<210> SEQ ID NO 12
<211> LENGTH: 8
<212> TYPE: PRT
<213> ORGANISM: Murinae gen. sp.

<400> SEQUENCE: 12

Cys Val Lys Pro Gly Gly Asp Tyr
1               5

<210> SEQ ID NO 13
<211> LENGTH: 34
<212> TYPE: DNA
<213> ORGANISM: Human cytomegalovirus

<400> SEQUENCE: 13
gtcactagat ctgccgttga cattgattat tgac                              34

<210> SEQ ID NO 14
<211> LENGTH: 37
<212> TYPE: DNA
<213> ORGANISM: Bos taurus

<400> SEQUENCE: 14
acactgagat cttccccagc atgcctgcta ttgtctt                           37
```